United States Patent
Timp et al.

(10) Patent No.: US 8,394,584 B2
(45) Date of Patent: Mar. 12, 2013

(54) DETECTING AND SORTING METHYLATED DNA USING A SYNTHETIC NANOPORE

(75) Inventors: Gregory Timp, South Bend, IN (US); Winston Timp, Baltimore, MD (US); Andrew Feinberg, Baltimore, MD (US); Utkur Mirsaidov, Urbana, IL (US)

(73) Assignees: The Board of Trustees of the University of Illinois, Urbana, IL (US); The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/133,300

(22) PCT Filed: Dec. 18, 2009

(86) PCT No.: PCT/US2009/068726
§ 371 (c)(1),
(2), (4) Date: Aug. 25, 2011

(87) PCT Pub. No.: WO2010/080617
PCT Pub. Date: Jul. 15, 2010

(65) Prior Publication Data
US 2012/0040343 A1 Feb. 16, 2012

Related U.S. Application Data

(60) Provisional application No. 61/139,056, filed on Dec. 19, 2008.

(51) Int. Cl.
*C12Q 1/68* (2006.01)
*C12P 19/34* (2006.01)
*C12M 1/34* (2006.01)
*C07H 21/02* (2006.01)
*C07H 19/00* (2006.01)

(52) U.S. Cl. ............ 435/6.1; 435/91.1; 435/287.2; 536/23.1; 536/28.54; 977/924

(58) Field of Classification Search ............ 435/6.1, 435/91.1, 287.2; 536/23.1, 28.54; 977/924
See application file for complete search history.

(56) References Cited

U.S. PATENT DOCUMENTS

| | | |
|---|---|---|
| 5,795,782 A | 8/1998 | Church et al. |
| 6,174,709 B1 | 1/2001 | Kenten et al. |
| 6,300,071 B1 | 10/2001 | Vuylsteke et al. |
| 6,605,432 B1 | 8/2003 | Huang |
| 6,693,051 B2 | 2/2004 | Muller et al. |
| 7,045,319 B2 | 5/2006 | Hanna |
| 7,144,701 B2 | 12/2006 | Huang |
| 7,186,512 B2 | 3/2007 | Martienssen et al. |
| 7,214,485 B2 | 5/2007 | Belinsky et al. |
| 7,226,738 B2 | 6/2007 | Hanna et al. |
| 7,358,048 B2 | 4/2008 | Baraby et al. |
| 7,432,050 B2 | 10/2008 | Markowitz |
| 2006/0183112 A1 | 8/2006 | Min et al. |
| 2009/0084688 A1 | 4/2009 | Leburton et al. |
| 2011/0226623 A1 | 9/2011 | Timp et al. |

FOREIGN PATENT DOCUMENTS

| | | | |
|---|---|---|---|
| WO | WO2008/079169 | * | 7/2008 |
| WO | WO 2010/080617 | | 7/2010 |

OTHER PUBLICATIONS

Wang et al, BRCA1 promoter methylation predicts adverse ovarian cancer prognosis, 2006, Gynecologic Oncology, 101, 403-410.*
Akeson et al. (Dec. 1999) "Microsecond Time-Scale Discrimination Among Segments within Single RNA Molecules," *Biophys. J.* 77(6):3227-3233.
Akiyama et al. (Dec. 2003) "GATA-4 and GATA-5 Transcription Factor Genes and Potential Downstream Antitumor Target Genes are Epigeneticallu Silenced in Colorectal and Gastric Cancer," *Mol. Cell. Biol.* 23(23):8429-8439.
Akselrod et al. (Nov. 2006) "Laser-Guided Assembly of Heterotypic 3D Living Cell Microarrays," *Biophys. J.* 91(9):3465-3473.
Aksimentiev et al. (2008) "Nanomedicine: Stretching Genes with a Synthetic Nanopore," Slides presented at the Center for Nanoscale Science and Technology, Nanotechnology Workshop 2008; Beckman Institute for Advanced Science and Technology; and the Micro and Nanotechnology Laboratory (MNTL) Auditorium, University of Illinois, Urbana, IL Sep. 4-5.
Aksimentiev et al. (Sep. 2004) "Microscopic Kinetics of DNA Translocation Through Synthetic Nanopores," *Biophys. J.* 87:2086-2097.
Aksimentiev et al. (Jun. 2005) "Imaging Alpha-Hemolysin with Molecular Dynamics: Ionic Conductance, Osmotic Permeability and the Electrostatic Potential Map," *Biophys. J.* 88:3745-3761.
Ashkenasy et al. (2005) "Recognizing a Single Base in an Individual DNA Strand: A Step Toward DNA Sequencing in Nanopores,"*Angew. Chem. Int. Ed. Engle.* 44:1401-1404.
Astier et al. (2006) "Toward Single Molecule DNA Sequencing: Direct Identification of Ribonuclease and Deoxyribonucleoside-Monophosphates by Using an Engineered Protein Nanopore Equipped with a Molecular Adapter," *J. Am. Chem. Soc.* 128(5):1705-1710.
Bachman et al. (Feb. 15, 1999) "Methylation-Associated Silencing of the Tissue Inhibitor of Metalloproteinase-3 Gene Suggests a Suppressor Role in Kidney, Brain, and Other Human Cancers," *Cancer Res.* 59(4):798-802.

(Continued)

*Primary Examiner* — Stephen Kapushoc
*Assistant Examiner* — Narayan Bhat
(74) *Attorney, Agent, or Firm* — Lathrop & Gage LLP

(57) ABSTRACT

Provided are methods for detecting, characterizing or separating DNA based on methylation. Heterogeneous DNA populations are separated based on DNA methylation by providing a membrane having a nanopore through which an electric field is applied. DNA of interest is introduced, and for a given threshold voltage across the nanopore, only DNA having a methylation parameter of interest may transit the pore, thereby facilitating detection, characterization, or separation of DNA based on methylation. The methods are optionally used to detect a disease state that is associated with DNA methylation including, but not limited to, cancer.

30 Claims, 4 Drawing Sheets

OTHER PUBLICATIONS

Badal et al. (Jun. 2003) "CpG Methylation of Human Papilomavirus Type 16 DNA in Cervical Cancer Cell Lines and in Clinical Specimens: Genomic Hypomethylation Correlates with Carcinogenic Progression," *J. Virol.* 77(11):6227-6234.

Barski et al. (May 18, 2007) "High-Resolution Profiling of Histone Methylations in the Human Genome," *Cell* 129(4):823-837.

Baylay et al. (Sep. 13, 2001) "Stochastic Sensors Inspired by Biolog," *Nature* 413(6852)226-230.

Bejerano et al. (2004) "Into the Heart of Darkness: Large-Scale Clustering of Human Non-Coding DNA," *Bioinformatics* 20(1):i40-i48.

Bell, G. (May 12, 1978) "Models of the Specific Adhesion of Cells to Cells," *Science* 200:618-627.

Bell et al. (May 25, 2002) "Methylation of a CTCF-Dependent Boundary Controls Imprinted Expression of the IGF2 Gene," *Nature* 405:482-485.

Benner et al. (Jun. 2000) "Gene Expression Analysis by Massively Parallel Signature Sequencing (MPSS) on Microbead Arrays," *Nat. Biotechnol.* 18:630-634.

Birney et al. (Jun. 14, 2007) "Identification and Analysis of Functional Elements in 1% of the Human Genome by the ENCODE Pilot Project," *Nature* 447:799-816.

Bookout et al. (2006) "High-Throughput Real-Time Quantitative Reverse Transcription PCR," *Curr. Protocols Mol. Biol.* Ch. 15, unit 15 18.

Botstein et al. (1980) "Construction of a Genetic Linkage Map in Man Using Restriction Length Polymorphisms," *Am. J. Hum. Genet.* 32:314-331.

Branton et al. (Oct. 2008) "The Potential and Challenges of Nanopore Sequencing," *Nature Biotechnol.* 26(10):1146-1153.

Braslavski et al. (Apr. 1, 2001) "Sequence Information can be Obtained from Single DNA Molecules," *Proc. Nat. Acad. Sci. USA* 100(7):3960-3964.

Brena et al. (Dec. 2006) "Toward a Human Epigenome," *Nature Genetics* 38(12):1359-1360.

Bustamente et al. (2000) "Single-Molecule Studies of DNA Mechanics" *Curr. Opin. Struct. Biol.* 10:279-285.

Cady et al. (2003) "Nucleic Acid Purification using Microfabricated Silicon Structures," *Biosesnsors and Bioelectrics*19(1):59-66.

Callinan et al. (2006) "The Emerging Science of Epigenomics," *Human Mol. Gen.* 15:R95-R101.

Catteau et al. (2002) "BRCA1 Methylation: A Significant Role in Tumour Development," *Sem. Cancer Biol.* 12:359-371.

Chang et al. (Web Release Jul. 7, 2004) "DNA-Mediated Fluctuations in the Ionic Current Through Silicon Oxide Nanopore Channels," *Nano Lett.* 4(8):1551-1556.

Chazalviel, J.N. (1979) "Schottky Barrier Height and Reverse Current of the n-Si-Electrolyte Junction," *Surf. Sci.* 88:204-220.

Chemla et al. (Web Release Jun. 27, 2005) "Bias Voltage Dependent Electrochemical Impedance Spectroscopy of p and n-type Silicon Substrates," *Electrochimica Acta.* 51:665-676.

Chen et al. (Web Release Oct. 26, 2004) "Probing Single DNA Molecule Transport Using Fabricated Nanopores" *Nano Lett.* 4(11):2293-2298.

Chen et al. (Web Release Jan. 5, 2001) "Evidence that Silencing of the HPRT Promoter by DNA Methylation is Mediated by Critical CpG Sites," *J. Biol. Chem.* 276:320-328.

Cho et al. (2003) "Promoter Hypomethylation of a Novel Cancer/Testis Antigen Gene CAGE is Correlated with its Aberrant Expression and is Seen in Premalingnant Stage of Gastric Carcinoma," *Biochem. Biophys. Res. Commun.*307(1):52-63.

Clark et al. (1994) "High Sensitivity Mapping of Methylated Cytosines," *Nuc. Acids Res.*22 (15):2990-2997.

Clerke et al. (Apr. 2009) "Continuous Base Identification for Single-Molecule Nanopore DNA Sequencing," *Nat. Nanotechnol.* 4:265-270.

Cluzel-Schaumann et al. (Apr. 2000) "Mechanical Stability of Single DNA Molecules" *Biophysical J.* 78:1997-2006.

Cockroft et al. (2008) "A Single —Molecule Nanopore Device Detects DNA Polymerase Activity with Single-Nucleotide Resolution," *J. Am. Chem. Soc.* 130(3):818-820.

Comer et al. (Jan. 2009) "Microscopic Mechanics of Hairpin DNA Translocation Through Synthetic Nanopores," *Biophys. J.* 96:593-608.

Costello et al. (Feb. 2000) "Aberrant CpG-Island Methylation has Non-Random and Tumour-Type- Specific Patterns," *Nature Genet.* 24:132-138.

Cross et al. (Mar. 1994) "Purification of CpG Islands Using a Methylated DNA Binding Column," *Nat. Genet.* 6(3):236-244.

Cruz-Chu et al. (Web Release Pct. 13, 2006) "Water-Silica Force Field for Simulating Nanodevices," *J. Phys. Chem. B* 110:21497-21508.

Cruz-Chu et al. (2009) "Molecular Control of Ionic Conduction in Polymer Nanopores," *Faraday Disc.* 143:47-62.

Deamer et al. (Web Release Sep. 27, 2002) "Characterization of Nucleic Acids by Nanopore Analysis," *Acc. Chem. Res.* 35(10):817-825.

Derreumaux et al. (2001) "Impact of CpG Methylation on Structure, Dynamics and Salvation of cAMP DNA Responsive Element," *Nuc. Acids Res.*29(11):2314-2326.

Dicke, R.H. (Jul. 1946) "The Measurement of Thermal Radiation at Microwave Frequencies," *Rev. Sci. Instrum.* 17(7):268-275.

Dimitrov et al. (2006) "Exploring the Prospects for a Nanometer-Scale Gene Chip," *IEDM Proceedings* :169-172.

Dimitrov et al. (2010) "Nanopores in Solid-State Membranes Engineered for Single-Molecule Detection," *Nanotechnology* 21:065502.

Dimitriov et al. (2005) "High Performance, sub-50nm MOSFETS for mixed signal Applications," *IEDM Tech Digest* :213-216.

Dimitrov et al. (2008) "Small-Signal Performance and Modeling of Sub-50nm nMOSFETs with FT above 460-GHz," *Solid State Electronics* 52:899-908.

Dimitrov et al. (2005) "High-Performance, sub 50nm nMOSFET with 290-GHz ft for Mixed Signam Amplification," *IEDM 2005 Proceedings*.

Dorset et al. (1975) "Excess Electrical Noie During Current Flow Through Porous Membranes Separating Ionic Solutions," *J. Membr. Biol.* 21: 291-309.

Dorvel et al. (2009) "Analyzing the Forces Binding a Restriction Endonuclease to DNA Using a Synthetic Nanopore," *Nuc. Acids Res.* 37(12):4170-4179.

Drmanac, R. (2001) "DNA Sequencing by Hybridization with Arrays of Samples or Probes," *Methods Mol. Biol.* 170:173-179.

Dudko et al. (Mar. 17, 2006) "Intrinsic Rates and Activation Free Energies from Single Molecule Pulling Experiments," *Phys. Rev. Lett.* 96:108101.

Dudko et al. (Jun. 2007) "Extraction Kinetics from Single-Molecule Force Spectroscopy: Nanopore Unzipping of DNA Hairpins," *Biophys. J.* 92:4188-4195.

Eads et al. (Apr. 15, 2000) "MethylLight: a High-Throughput Assay T-Measure DNA Methylation," *Nuc. Acids Res.* 28(8):e32-00.

Eckhardt et al. (Dec. 2006) "DNA Methylation Profiling of Human Chromosomes 6,20,22" *Nature Genet.* 38:1378-1385.

Esteller et al. (May 1, 2000) "Inactivation of the DNA Repair Gene O6- Methylguanine-DNA Methyltransferase by Promoter Hypermethylation is Associated with G to A Mutations in K-ras in Colorectal Tumorigenesis," *Cancer Res.* 60(9):2368-2371.

Esteller et al. (Apr. 5, 2000) "Promoter Hypermethylation and BRCA1 Inactiveation in Sporadic Breast and Ovarian Tumors," *J. Nat. Cancer Inst.* 92(7):564-569.

Esteller et al. (2000) "Epigenetic Inactivation of LKB1 in Primary Tumors Associated with Peutz-Jeghers Syndrom," *Oncogene* 19(1):164-168.

Esteller et al. (Apr. 15, 2001) "A Gene Hypermethylation Profile of Human Cancer," *Cancer Res.* 61(8):3225-3229.

Evans et al. (Apr. 1997) "Dynamic Strength of Molecular Adhesion Bonds," *Biophys. J.* 72:1541-1555.

Evans et al. (Jun. 1995) "Sensitive Force Technique to Probe Molecular Adhesion and Structural Linkages at Biological Interfaces," *Biophys. J.* 68:2580-2587.

Evans et al. (Apr. 1991) "Detachment of Agglutinin-Bonded Red Blood Cells. I. Forced to Rupture Molecular-Point Attachments," *Biophys. J.* 59:838-848.

Feinberg et al. (Feb. 28, 1983) "Hypomethylation of Ras Oncogenes in Primary Human Cancers," *Biochem. Biophys. Res. Commun.* 111(1):47-54.

Fenley et al (2003) "Approach to the Limit of Counterion Condensation," *Biopolymers* 30(13-14):1191-1203.

Ferguson et al. (Jun. 1, 1995) "Demethylation of the Estrogen Receptor Gene in Estrogen Receptor-Negative Breast Cancer Cells Can Reactivate Estrogen Receptor Gene Expression," *Cancer Res.* 55(11):2279-22283.

Ferreira et al. (Nov. 2006) "Enthalpy of the B-to-Z Conformational Transition of a DNA Oligonucleotide Determined by Isothermal Titration Calorimetry," *Biophysical Journal* 91(9):3383.

Fischbein et al. (Web Release Apr. 17, 2007) "Sub-10 nm Device Fabrication in a Transmission Electron Microscope," *Nano Lett.* 7(5):1329-1337.

Fisher et al. (Sep. 2000) "Stretching Single Molecules into Novel Conformation Using the Atomic Force Microscope," *Nature Struct. Bio.* 7(9):719-724.

Fologea et al. (Web Release Aug. 9, 2005) "Slowing DNA Translocation in a Solid-State Nanopore," *Nano Lett.* 5(9):1734-1737.

Fraga et al. (2003) "The Affinity of Different MBD Proteins for a Specific Methylated Locus Depends on their Intrinsic Binding Properties," *Nuc. Acids Res.* 31(6):1765-1774.

Frederick et al. (Nov. 25, 1988) "Methylation of EcoRI Recognition Site Does Not Alter DNA Conformation: The Crystal Structure of s(CGCGAm6ATTCGCG) at 2.0-A Resolution," *J. Biol. Chem.* 263(33):17872-17879.

Friedsam et al. (2003) "Dynamic Single-Molecule Force Spectroscopy: Bond Rupture Analysis with Variable Spacer Length," *J. Phys. Cond. Matter* 15:S1709-S1723.

Furini et al. (Sep. 2008) "Model-Based Prediction of the α-Hemolysin Structure in the Hexameric State," *Biophys. J.* 95:2265-2274.

Geahigan et al. (Web Release Mar. 30, 2000) "The Dynamic Impact of CpG Methylation in DNA," *Biochemistry* 39:4939-4946.

Gill et al. (Jun. 2, 2006) "Metagenomic Analysis of the Human Distal Gut Microbiome," *Science* 312:1355-1359.

Goychuk et al. (Mar. 19, 2002) "Ion Channel Gating: A First-Passage Time Analysis of the Kramers Type," *Proc. Nat. Acad. Sci. USA* 99:3552.

Gracheva et al. (2006) "Simulation of the Electric Response of DNA Translocation through a Semiconductor Nanopore-Capacitor" *Nanotechnol* 17:622-633.

Gracheva et al. (2006) "Electrical Signatures of Single-Stranded DNA Translocation through a Semiconductor Nanopore-Capacitor" *Nanotechnol* 17:3160-3165.

Grubmuller et al. (Feb. 16, 1996) "Ligand Binding: Molecular Mechanics Calculation of the Streptavin Biotin Rupture Force," *Science* 271:997-999.

Guéron et al. (Feb. 2000) A Unified Theory of the B-Z Transition of DNA in High and Low Concentrations of Multivalent Ions, *Biophysical J.* 78(2):1070-1083.

Guthold et al. (2001) "The Rules are Changing: Force Measurements on Single Molecules and How they Relate to Bulk Reaction Kinetics and Energies," *Biomedical Microdevices* 3(1):9-18.

Gyurcsányi, R.E. (2008) "Chemically-Modified Nanopores for Sensing," *Anal. Chem.* 27(7):627-639.

Ha et al. (Oct. 10, 2002) "Initiation and Re-Initiation of DNA Unwinding by the *Escherichia coli* Rep Helicase," *Nature* 419:638-641.

Hark et al. (2000) "CTCF Mediates Methylation-Sensitive Enhancer Blocking Activity at the H19/Igf2 Locus," *Nature* 405(6785):486-489.

Harris et al. (2008) "Single-Molecule DNA Sequencing of a Viral Genome," *Science* 320:106-109.

Heinemann et al. (1992) "CCAGGC-m5C-TGC. Helical Fine Structure, Hydration, and Comparison with CCAGGCCTGG," *J. Biological Chem.* 267(11):7332-7341.

Heng et al. (Aug. 2004) "Sizing DNA Using a Nanometer-Diameter Pore," *Biophys. J.* 87(4):2905-2911.

Heng et al. (2005) "Beyond the Gene Chip," *Bell Labs Tech. J.* 10(3):5-22.

Heng et al. (Oct. 2005) "Stretching *DNA* using the Electric Field in a Synthetic Nanopore," *NanoLet.* 5(10):1883-1888.

Heng et al. (Feb. 2006) "The Electromechanics of DNA in a Synthetic Nanopore," *Biophys. J.* 90(3):1098-1106.

Henrickson et al. (Oct. 2000) "Driven DNA Transport into an Asymmetric Nanometer-Scale Pore," *Phys. Rev. Lett.* 85(14):3057-3060.

Herman et al. (Jul. 1994) "Silencing of the VHL Tumor-Suppressor Gene by DNA Methylation in Renal Carcinoma," *Proc. Nat. Acad. Sci. USA* 91(21):9700-9704.

Herman et al. (Sep. 1996) "Methylation-Specific PCR: A Novel PCR Assay for Methylation Status of CpG Islands," *Nat. Acad. Sci.* 93:9821-9826.

Herman et al. (1997) "Distinct Patterns of Inactivation of P15INK4B and p16INK4A Characterize the Major Types of Hemtological Malignancies," *Cancer Res.*57(5):837-841.

Heymann et al. (Jul. 1999) "Elastic Properties of Poly Ethelene Glycol Studied by Molecular Dynamics Stretching Simulation," *Chem. Phys. Lett.* 307(5-6):425-432.

Heymann et al. (Apr. 1999) "AN02/DNP-hapten Unbinding Forces Studies by Molecular Dynamics Atomic Force Microscopy Simulations," *Chem. Phys. Lett.* 303(1-2):1-9.

Ho et al. (Feb. 2008) "MeCP2 Binding to DNA Depends upon Hydration at Methyl-CpG," *Mol. Cell* 29:525-531.

Ho et al. (Jul. 2005) "Electrolytic Transport Through a Synthetic Nanometer-Diameter Pore," *Proc. Nat. Acad. Sci. USA* 102(30):10445-10450.

Hodges-Garcia et al. (Jan. 1995) "Investigation of the Influence of Cytosine Methylation on DNA Flexibility," *J. Biol. Chem.* 270(1):197-201.

Hodges-Garcia et al. (Aug. 1992) "Cytosine Methylation can Induce Local Distortions in the Structure of Duplex DNA," *Biochemistry* 31(33)7595-7599.

Hooge et al. (1971) "Fluctuations with a $1/f$ Spectrum in the Conductance of Ionic Solutions and in the Voltage of Concentration Cells," *Philips Res. Reports* 26:77-.

Hornblower et al. (Apr. 2007) "Single-Molecule Analysis of DNA-Protein Complexes Using Nanopores," *Nature Meth.* 4(4):315-317.

Hseih, C.L. (Oct. 1997) "Stability of Patch Methylation and its Impact in Regions of Transcriptional Initiation and Elongation," *Mol. Cell. Biol.* 17(10):5897-5904.

Hummer et al. (Jul. 2003) "Kinetics from Nonequilibrium Single-Molecule Pulling Experiments," *Biophys. J.* 85(1):5-15.

Im et al. (Aug. 2000) A Grand Canonical Monte Carlo-Brownian Dynamics Algorithm for Simulating Ion Channels, *Biophys. J.* 79(2):788-801.

Im et al. (2002) "Ions and Counterions in a Biological Channel: A Molecular Dynamics Study of OmpF Porin from *Escherichia coli* in an Explicit Membrane with 1M KCl Aqueous Salt Solution," *J. Mol. Biol.* 319:1177-1197.

International Search Report and Written Opinion, Corresponding to International Application No. PCT/US2009/068726, Mailed Sep. 27, 2010.

Irizarry et al. (May 2008) "Comprehensive High-Throughput Arrays for Relative Methylation (CHARM)," *Genome Res.* 18(5):780-790.

Issa, J.P. (Dec. 2005) "CpG Island Methylator Phenotype in Cancer," *Nature Rev.* 4:988-993.

Jeltsch, A. (2002) "Beyond Watson and Crick: DNA Methylation and Molecular Enzymology of DNA Methytransferases," *Chem. Bio. Chem.* 3:274-293.

Jeltsch et al. (Aug. 1994) "Pausing of the Restriction Endonuclease EcoRi During Linear Diffusion on DNA," *Biochemistry* 33(34):10215-10219.

Jen-Jaconsen, L. (1997) "Protein-DNA Recognition Complexes: Conservation of Structure and Binding Energy in the Transition State," *Biopolymers* 44:153-180.

Jeong et al. (Oct. 2002) "A Study of Sapphire Etching Characteristics Using BCI3- Based Inductivity Coupled Plasmas," *Jap. J. Appl. Phys.* 41(10):6206-6208.

Johnson et al. (Jun. 2007) "Genome-Wide Mapping of in Vivo Protein-Dna Interactions," *Science* 316:1497-1502.

Jones et al. (Feb. 2007) "The Epigenomics of Cancer," *Cell.* 128:683-692.

Jones et. al. (Jun. 2002) "The Fundamental Role of Epigenetic Events in Cancer," *Nature Rev. Gen.* 3:415-428.

Kane et al. (Mar. 1997) "Methylation of the hMLH1 Promoter Correlates with the Lack of Expression of hMLH1 in Sporadic Colon Tumors and Mismatch Repair-Defective Human Tumor Cell Lines," *Cancer Res.* 57(5):808-811.

Kaneda et al. (Dec. 2007) "Enhanced Sensitivity to IGF-II Signaling Links Loss of Imprinting of *IGF2* to Increased Cell Proliferation and Tumor Risk," *Proc. Nat. Acad. Sci. USA* 104(52):20926-20931.

Kasianowicz et al. (Nov. 1996) "Characterization of Individual Polynucleotide Molecules Using a Membrane Channel," *Proc. Nat. Acad. Sci.USA* 93(24):1377013773.

Keyser et al. (Jul. 2006) "Direct Force Measurements of DNA in a Solid-State Nanopore," *Nature Phys.* 2:473-475.

Khulan et al. (2006) "Comprehensive Isoschizomer Profiling of Cytosine Methylation: The HELP Assay," *Genome Res.* 16(8):1046-1055.

Kim et al. (2007) "SNP Genotyping: Technologies and Biomedical Applications," *Ann. Rev. Biomed. Eng.* 9:289-320.

Kinoshita et al. (Jul. 2000) "Methylation of the Androgen Receptor Minimal Promoter Silences Transcription in Human Prostate Cancer," *Cancer Res.* 60(13):3623-3630.

Kruger et al. (1995) "McrB: A Prokaryotic Protein Specifically Recognizing DNA Containing Modified Cytosine Residues," *EMBO* 14(11):2661-2669.

Laird, P.W. (Apr. 2003) "The Power and the Promise of DNA Methylation Markers," *Nature Rev.* 3:253-266.

Lander et al. (Feb. 2001) "Initial Sequencing and Analysis of the Human Genome," *Nature* 409:860-921.

Lederer et al. (Aug. 1986) "Solution Structure of a Short DNA Fragment Studied by Neutron-Scattering," *Eur. J. Biochem.* 161(1):191-196.

Lee et al. (Web Release Jul. 3, 2001) "Controlling the Transport Properties of Gold Nanotubule Membranes Using Chemisorbed Thiols," *Chem. Mater.* 13:3236-3244.

Lefebvre et al. (Feb. 1995) "Sequence Dependent Effects of CpG Cytosine Methylation: A Joint H-NMR and P-NMR Study," *Eur. J. Biochem.* 229:445-454.

Lesser et al. (1990) "The Energetic Basis of Specificity in the *Eco*-Ri Endonuclease-*DNA* Interaction," *Science* 250:776-786.

Li et al. (Jul. 2001) "Ion-Beam Sculpting at Nanometre Length Scales," *Nature* 412:166-169.

Likharev et al. (Apr. 1999) "Single-Electron Devices and Their Applications," *Proceedings of the IEEE* 87(4):606-632.

Lin et al. (2011) "Imaging in Real-Time with FRET the Redox Response of Tumorigenic Cells to Glutathione Pertuurbations in a Microscale Flow," *Integr. Biol.* 3:208-217.

Lippman et al. (Mar. 2005) "Profiling DNA Meththylation Patterns Using Genomic Tiling Microarrays" *Nat Meth* 2(3):219224.

Luan et al. (Sep. 2008) "Strain Softening in Stretched DNA," *Phys. Rev. Lett.* 101(11):118101.

Madou et al. (Nov. 1980) "The Silicon/Silica Electrode," *Phys. Stat. Sol. A* 57:705712.

Manning (1978) "The Molecular Theory of Polyelectrolyte Solutions with Applications to the Electrostatic Properties of Polynucleotides," *Q Rev, Biophys.* 11(2):179-246.

Marcus et al. (May 2006) "Microfluidic Single-Cell MRNA Isolation and Analysis," *Anal. Chem.* 78(9):3084-3089.

Mardis, E.R. (2008) "The Impact of Next-Generation Sequencing Technology on Genetics," *Trends Genet.* 24(3):133-141.

Martin et al. (2001) "Controlling Ion Transport Selectivity in Gold Nanotubule Membranes," *Adv. Mater.* 13: 1351-1362.

Marziali et al. (2001) "New DNA Sequencing Methods," *Ann. Rev. Biomed. Eng.* 3:195-233.

Mathé et al. (Nov. 2004) "Nanopore Unzipping of Individual DNA Hairpin Molecules," *Biophys. J.* 87:3205-3212.

Mathé et al. (Jan. 2006) "Equilibrium and Irreversible Unzipping of DNA in a Nanopore," *Europhyd. Lett.* 73(1):128-134.

McGillivray et al. (1980) "Dual-Path Capacitance Compensation Network for Microelectrode Recordings," *Am. J. Physiol.* 238:H930-H931.

Meints et al. (Sep. 2001) "Dynamic Impact of Methylation at the M *Hhal*Target Site: A Solid-State Deuterium NMR Study," *Biochemistry* 40(41)12436-12443.

Melin et al. (2007) "Microfluidic Large-Scale Integration: The Evolution of Design Rules for Biological Automation," *Ann. Rev. Biophys. Biomol. Struct.* 36:213-231.

Miranda et al. (2007) "DNA Methylation: The Nuts and Bolts of Repression," *J. Cell. Physiol.* 213:384-390.

Mirsaidov et al. (2009) "Nanoelectromechanics of Methylated DNA in a Synthetic Nanopore," *Biophys. J. Lett.* 96(4):L32-L34.

Mirsaidov et al. (2010) "Slowing the Translocation of Double-Stranded DNA using a Nanopore Smaller that the Double Hlix," *Nanotechnology* 21:395501.

Mirsidov et al. (2010) "Molecular Diagnostics for Personal Medicine Using a Nanopore," *Advanced review* 2:367-381.

Mirsaidov (2008) "Optimal Optical Trap for Bacterial Viability," *Phys. Rev. E.* 78(2):021910.

Mirsaidov et al. (Oct. 2008) "Live Cell Lithography: Using Optical Tweezers to Create Synthetic Tissues," *Lab on a Chip* 8:2174-2181.

Mitra et al. (May 2003) "Digital Genotyping and Haplotyping with Polumerase Colonies," *Proc. Nat. Acad. Sci. USA* 100(10):5926-5931.

Morozova et al. (2008) "Applications of Next-Generation Sequencing Technologies in Functional Genomics," *Genomics* 92(5):255-264.

Muthukumar et al. (Dec. 2006) "Simulation of Polymer Translocation Through Protein Channels," *Proc. Nat. Acad. Sci. USA* 103(4):5273-5278.

Nair et al. (Jun. 2006) "Performance Limits of Nanobiosensors," *Appl. Phys. Lett.* 88:233120.

Nakamura et al. (1998) "Hypermethylation of the Metastasis-Associated S100A4 Gene Correlates with Gene Activation in Human Colon Adenocarcinoma Cell Lines," *Clin. Exp. Metastasis* 16(5):471-479.

Nakane et al. (2002) "Evaluation of Nanopores as Candidates for Electronic Analyte Detection," *Electrophoresis* 23(16):2592-2601.

Nakayama et al. (1998) "Hypomethylation Status of CpG Sites at the Promoter Region and Overexpression of the Human MDR1 Gene in Acute Myeloid Leukemias," *Blood* 92(11):4296-4307.

Nathan et al. (2002) "Bending and Flexibility of Methylated and Unmethylated EcoRI DNA," *J. Mol. Biol.* 316:7-17.

Nilsson et al. (2006) "Localized Functionalization of Single Nanopores," *Adv. Mater.* 18:427-431.

Noskov et al. (Oct. 2004) "Ion Permeation through the α-Hemolysin Channel: Theoretical Studies Based on Brownian Dynamics and Poisson-Nernst-Plank Electrodiffusion Theory," *Biophys. J.* 87:2299-2309.

Ohshiro et al. (Jan. 2006) "Complimentary Base-Pair-Facilitated Electron Tunneling for Electrically Pinpointing Complementary Nucleobases," *Proc. Nat. Acad. Sci.* 103(1):10-14.

Ohtanifujita et al. (1993) "CpG Methylation Inactivates the Promoter Activity of the Human Retinoblastoma Tumor-Suppressor Gene," *Oncogene* 8(4):1063-1067.

Ooi et al. (Jun. 2008) "The Colorful History of Active DNA Demethylation," *Cell* 133(7):1145-1148.

Ottow et al. (1998) "Determination of Flat-Band Potentials of Silicon Electrodes in HF by Means of AC Resistance Measurements," *J. Electroanalytical Chem.* 455:29-37.

Packer et al. (2002) "ParmGKB: The Pharmacogentics Knowledge Base," *Nuc. Acids Res.* 30(3):158-162.

Paegel et al. (2003) "Microfluidic Devices for DNA Sequencing: Sample Preparation and Electrophoretic Analysis," *Curr. Opin. Biotech.* 14:42-50.

Paez et al. (Jun. 2004) "EGFR Mutations in Lung Cancer: Correlation with Clinical response to Gefitinib Therapy," *Science* 304:1497-1500.

Panne et al. (1999) "The McrBC Endonuclease Translocates DNA in a Reaction Dependent on GTP Hydrolysis," *J. Mol. Biol.* 290(1):49-60.

Pearlman et al. (1990) "The Calculated Free Energy Effets of 5-Methyl Cytosine on the B to Z Transition in DNA," *Biopolymers* 29(8-9):1193-1209.

Phillips et al. (2005) "Scalable Molecular Dynamics with NAMD," *J. Comp. Chem.* 26:1781-1802.

Ramsahoye et al. (May 2000) "Non-CpG Methylation is Prevalent in Embryonic Stem Cells and May be Mediated by DNA Methyltransferase 3a," *Proc. Nat. Acad. Sci. USA* 97(10):5237-5242.

Rauch et al. (2003) "C5 Methylation of Cytosine in B-DNA Thermodynamically and Kinetically Stabilizes BI" *J. Am. Chem. Soc.* 125(49):14990-14991.

Rauch et al. (2005) "Towards an Understanding of DNA Recognition by the Methyl CpG Binding Domain 1," *J. Biomol. Struct. Dyn.* 22(6):695-706.

Reu et al. (Mar. 2006) "Expression of RASSF1A, an Epigenetically Silenced Tumor Suppressor, Overcomes Resistance to Apoptosis Induction by Interferons," *Cancer Res.* 66(5):2785-2793.

Rivetti et al. (Mar. 1998) "Polymer Chain Statistics and Conformational Analysis of DNA Molecules with Bends or Sections of Difference Flexibility," *J. Mol. Biol.* 280:41-59.

Robertson, K.D. (May 2005) "DNA Methylation and Human Disease," *Nature Rev.* 6:597-610.

Robertson et al. (2007) "Single-Molecule Mass Spectrometry in Solution Using a Solitary Nanopore," *Proc. Nat. Acad. Sci. USA* 104(20):8207-8211.

Ronaghi, M. (2001) "Pyrosequencing Sheds Light on DNA Sequencing," *Genome Res.* 11:3-11.

Roux, B. (1995) "The Calculation of the Potential of Mean Force Using Computer Simulations," *Comp. Phys. Comm.* 91:275-282.

Rouzina et al. (Feb. 2001) "Force Induced Melting of DNA Double Helix 2. Effect of Solution Conditions" *Biophysical J.* 80:894-900.

Rouzina et al. (2001) "Force Induced Melting of the DNA Double Helix 1. Thermodynamic Anallysis," *Biophys. J.* 80:882-893.

Salisbury, M.W. (2003) "Fourteen Sequencing Innovations that Could Change the way you Work," *Genome Technol.* 35:40-47.

Sanger et al. (1977) "DNA Sequencing with Chine-Terminating Inhibitors," *Proc. Nat. Acad. Sci. USA* 74(12):5463-5467.

Sauer-Budge et al. (Jun. 2003) "Unzipping Kinetics of Double-Stranded DNA in a Nanopore," *Phys. Rev. Lett.* 90(23):238101.

Scofield, J.H. (Feb. 1994) "Frequency-Domain Description of a Lock-in Amplifier," *Am. J. Phys.* 62(2):129-133.

Scott et al. (2008) "3D Hydrodynamic Focusing in a Microfluidic Coulter Counter," *Rev. Sci. Instrum.* 79:046104.

Shaw et al. (2007) "Anton, A Special-Purpose Machine for Molecular Dynamics Simulation," International Symposium on Computer Architecture, ACM 1-12.

Shendure et al. (May 2004) "Advanced Sequencing Technologies: Methods and Goals," *Nat. Rev. Genet.* 5(5):335-344.

Sigalov et al. (Web Release Dec. 11, 2007) "Detection of DNA Sequences Using an Alternating Electric Fields in a Nanopore Capacitor," *Nano Lett.* 8(1):56-63 Plus Supporting Information.

Siwy et al. (Nov. 2002) "Fabrication of a Synthetic Nanopore Ion Pump," *Phys. Rev. Lett.* 89(19):198103.

Smeets et al. (Jan. 2008) "Noise in Solid-State Nanopores," *Proc. Nat. Acad. Sci.* 105(2):417-421.

Smeets et al. (2009) "Low-Frequency Noise in Solid-State Nanopores," *Nanotechnology* 20:095501.

Smeets et al. (2006) "Salt Dependence of Ion Transport and DNA Translocation Through Solid-State Nanopores," *Nano Lett.* 6(1):89-95.

Smet et al. (Jul. 1996) "The Activation of Human Gene MAGE-1 in Tumor Cells is Correlated with Genome-Wide Demethylation," *Proc. Nat. Acad. Sci. USA* 93(14):7149-7153.

Smith et al (Feb. 1996) "Overstretching B-DNA: The Elastic Response of Individual Double-Stranded and Single-Stranded DNA Molecules" *Science* 271:795-799.

Sonnefeld et al. (Jul. 2001) "Determination of Electric Double Layer Parameters for Spherical Silica Particles under Application of the Triple Layer Model using Surface Charge Density Data and Results of Electrokinetic Sonic Amplitude Measurements," *Colloid Surf. A-Physiochm. Eng. Asp.* 195:215.

Stein et al. (2001) "Ion-Beam Sculpting at Nanometre Length Scales," *Nature* 412:166-169.

Stellwagon et al. (2003) "Probing the Electrostatic Shielding of DNA with Capillary Electrophoresis," *Biophysical J.* 84(3):1855-1866.

Stewart et al. (2000) "Methyl-Specific DNA Binding by McrBC, A Modification-Dependent Restriction Enzyme," *J. Mol. Biol.* 298:611-622.

Stoddarrt et al. (2009) "Single-Nucleotide Discrimination in Immobilized DNA Oligonucleotides with a Biological Nanopore," *Proc. Nat. Acad. Sci. USA* 106(19):7702-7707.

Storm et al. (Jul. 2003) "Fabrication of Solid-State Nanopores with Single-Nanometre Precision," *Nature Materials* 2(8):537-540.

Storm et al. (2005) "Fast DNA Translocation Through a Solid-State Nanopore," *Nano Lett.* 5(7):1193-1197.

Storm et al. (2005) "Translocation of Double-Strand DNA Through a Silicon Oxide Nanopore," *Phys Rev E.* 71: 051903-051910.

Suzuki et al. (Apr. 2004) "Epigenetic Inactivation of SFRP Genes Allows Constitutive WNT Signaling in Colorectal Cancer," *Nature Genet.* 36(4):417-422.

Tabard-Cossa et al. (Jun. 29, 2007) "Noise Analysis and reduction in Solid-State Nanopores," *Nanotech* 18:305505.

Takai et al. (Mar. 2002) "Comprehensive Analysis of CpG Islands in Human Chromosomes 21 and 22," *Proc. Nat. Acad. Sci. USA* 99(6):3740-3745.

Tardella et al. (Aug. 1985) "Highly Accumulated Electron Layer at a Semiconductor/Electrolyte Interface," *Phys. Rev. B.* 32(4):2439-2448.

Thorisson et al. (2005) "The International HapMap Project Web Site," *Genome Res.* 15:1592-1593.

Timp et al. (1999) "Nanoelectronics for Advanced Computation and Communications," In; *Nanotechnology* Timp, G. ed., Springer-Verlag, pp. 7-89.

Timp, G. (1998) "Progress Toward 10nm CMOS Devices," *Proc. IEDM* 98:615-618.

Timp et al. (2009) "Jamming Prokaryotic Cell-to-Cell Communications in a Model Biofilm," *Lab Chip* 9:925-934.

Timp et al. (May 2010) "Nanopore Sequencing: Electrical Measurements of the Code of Life," *IEEE Tran. Nanotechnol.* 9(3):281-294.

Van Dorp et al. (Mar. 2009) "Origin of the Electrophoretic Force on DNA in Solid-State Nanopores," *Nature Phys.* 5: 347-351.

Venter et al. (Feb. 2001) "The Sequence of Human Genome," *Science* 291:1304-1351.

Wang et al. (2006) "Fabrication of Patterns Sapphire Substrate by Wet Chemical Etching for Maskless Lateral Overgrowth of GaN," *J. Electrochem. Soc.* 153(3):C182-C185.

Wanunu et al. (2007) "Chemically Modified Solid-State Nanopores," *Nano Lett.* 7(6):1580-1585.

Weber et al. (Aug. 2005) "Chromosome-Wide and Promoter Specific Analyses Identify Sites of Differential DNA Methylation in Normal and Transformed Human Cells," *Nature Genetics* 37(8):853-862.

Weber et al. (Apr. 2007) "Distribution, Silencing Potential and Evolutionary Impact of Promoter DNA Methylation in the Human Genome," *Nature Genetics* 39(4):457-466.

William et al. (Apr. 2001) "Entropy and Heat Capacity of DNA Melting from Temperature Dependence of Single Molecule Stretching," *Biophys. J.* 80:1932-1939.

William et al. (Feb. 2001) "Effect of pH on the Overstretching Transition of Double-Stranded DNA: Evidence of Force-Induced DNA Melting," *Biophysical J* 80:874-881.

Wood et al. (Nov. 2007) "The Genomic Landscapes of Human Breast and Colorectal Cancers," *Science* 318:1108-1113.

Woodin, T. (2005) "Trends in Funding Science Education, 1994-2004," *Biochem. Mol. Biol. Ed.* 33(3):211-216.

Wu et al. (Dec. 2005) "Hypomethylation-Linked Activation of PAX2 Mediates Tamoxifen-Stimulated Endometrial Carcinogenesis," *Nature* 438(7070):981-987.

Xiong et al. (Apr. 1997) COBRA: A Sensitive and Quantitative DNA Methylation Assay *Nucleic Acids Res.* 25(12):2532-2534.

Yang et al. (Aug. 2005) "Determination of Protein-DNA Binding Constants and Specificities from Statistical Analyses of Single Molecules: MutS-DNA Interactions," *Nuc. Acids Res.* 33(13):4322-4344.

Yoder et al. (Aug. 1997) "Cytosine Methylation and the Ecology of Intragenomic Parasites," *TIG* 13(8):335-340.

Yuan et al. (2003) "Energy Landscape of Streptavidin Biotin Complexes Measured by Atomic Force Microscopy," *Biochemistry* 39(33):10219-10223.

Zhao et al. (2007) "Detecting SNPs Using a Synthetic Nanopore," *Nano Letters* 7(6):1680-1685.

Zhao et al. (Oct. 2008) "Stretching and Unzipping Nucleic Acid Hairpins Using a Synthetic Nanopore," *Nuc. Acids Res.* 36(5):1532-1541.

Zhumd et al. (1998) "Evaluation of Surface Ionization Parameters from AFM Data," *J. Colloid Interface Sci.* 207:332-343.

Applied Biosystems (2009) "The SOLiD 3 System: Enabling the Next Generation of Science," In; Applied Biosystems.

\* cited by examiner

SEQUENCE LISTING

<160> NUMBER OF SEQ ID NOS: 10

<210> SEQ ID NO 1
<211> LENGTH: 88
<212> TYPE: DNA
<213> ORGANISM: Homo sapiens

<400> SEQUENCE: 1
aggcgcgcct ttgggccacg atatatagga gtatgctgcc accgcgcggt agcatccgtt    60
cccttgttgc acataacagg gcgcgcct                                      88

<210> SEQ ID NO 2
<211> LENGTH: 88
<212> TYPE: DNA
<213> ORGANISM: Homo sapiens

<400> SEQUENCE: 2
aggcgcgccc tgttatgtgc aacaagggaa cggatgctac cgcgcggtgg cagcatactc    60
ctatatatcg tggcccaaag gcgcgcct                                      88

<210> SEQ ID NO 3
<211> LENGTH: 88
<212> TYPE: DNA
<213> ORGANISM: Homo sapiens
<220> FEATURE:
<221> NAME/KEY: modified_base
<222> LOCATION: (45)..(45)
<223> OTHER INFORMATION: m5c

<400> SEQUENCE: 3
aggcgcgcct ttgggccacg atatatagga gtatgctgcc accgcgcggt agcatccgtt    60
cccttgttgc acataacagg gcgcgcct                                      88

<210> SEQ ID NO 4
<211> LENGTH: 88
<212> TYPE: DNA
<213> ORGANISM: Homo sapiens
<220> FEATURE:
<221> NAME/KEY: modified_base
<222> LOCATION: (43)..(43)
<223> OTHER INFORMATION: m5c

<400> SEQUENCE: 4
aggcgcgccc tgttatgtgc aacaagggaa cggatgctac cgcgcggtgg cagcatactc    60
ctatatatcg tggcccaaag gcgcgcct                                      88

<210> SEQ ID NO 5
<211> LENGTH: 88
<212> TYPE: DNA
<213> ORGANISM: Homo sapiens
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (45)..(45)
<223> OTHER INFORMATION: m5c
<220> FEATURE:
<221> NAME/KEY: modified_base
<222> LOCATION: (47)..(47)

```
<223> OTHER INFORMATION: m5c
<220> FEATURE:
<221> NAME/KEY: modified_base
<222> LOCATION: (57)..(57)
<223> OTHER INFORMATION: m5c

<400> SEQUENCE: 5
aggcgcgcct ttgggccacg atatatagga gtatgctgcc accgcgcggt agcatccgtt    60
cccttgttgc acataacagg gcgcgcct                                       88

<210> SEQ ID NO 6
<211> LENGTH: 93
<212> TYPE: DNA
<213> ORGANISM: Homo sapiens
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (41)..(41)
<223> OTHER INFORMATION: m5c
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (45)..(45)
<223> OTHER INFORMATION: m5c

<400> SEQUENCE: 6
aggcgcgccc tgttatgtgc aacaagggaa mcggatgcta cmcgmcgmcg gtggcagcat    60
actcctatat atmcgtggcc caaaggcgcg cct                                 93

<210> SEQ ID NO 7
<211> LENGTH: 90
<212> TYPE: DNA
<213> ORGANISM: Homo sapiens

<400> SEQUENCE: 7
ctgagaaacc ccacagcctg tcccccgtcc aggaagtctc agcgagctca cgccgcgcag    60
tcgcagtttt aatttatctg taattcccgc                                     90

<210> SEQ ID NO 8
<211> LENGTH: 90
<212> TYPE: DNA
<213> ORGANISM: Homo sapiens

<400> SEQUENCE: 8
gcgggaatta cagataaatt aaaactgcga ctgcgcggcg tgagctcgct gagacttcct    60
ggacggggga caggctgtgg ggtttctcag                                     90

<210> SEQ ID NO 9
<211> LENGTH: 90
<212> TYPE: DNA
<213> ORGANISM: Homo sapiens
<220> FEATURE:
<221> NAME/KEY: modified_base
<222> LOCATION: (26)..(26)
<223> OTHER INFORMATION: m5c
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (51)..(51)
```

```
<223> OTHER INFORMATION: m5c
<220> FEATURE:
<221> NAME/KEY: modified_base
<222> LOCATION: (54)..(54)
<223> OTHER INFORMATION: m5c
<220> FEATURE:
<221> NAME/KEY: modified_base
<222> LOCATION: (56)..(56)
<223> OTHER INFORMATION: m5c
<220> FEATURE:
<221> NAME/KEY: modified_base
<222> LOCATION: (62)..(62)
<223> OTHER INFORMATION: m5c

<400> SEQUENCE: 9
ctgagaaacc ccacagcctg tcccccgtcc aggaagtctc agcgagctca cgccgcgcag      60
tcgcagtttt aatttatctg taattcccgc                                      90

<210> SEQ ID NO 10
<211> LENGTH: 90
<212> TYPE: DNA
<213> ORGANISM: Homo sapiens
<220> FEATURE:
<221> NAME/KEY: modified_base
<222> LOCATION: (28)..(28)
<223> OTHER INFORMATION: m5c
<220> FEATURE:
<221> NAME/KEY: modified_base
<222> LOCATION: (34)..(34)
<223> OTHER INFORMATION: m5c
<220> FEATURE:
<221> NAME/KEY: modified_base
<222> LOCATION: (36)..(36)
<223> OTHER INFORMATION: m5c
<220> FEATURE:
<221> NAME/KEY: modified_base
<222> LOCATION: (39)..(39)
<223> OTHER INFORMATION: m5c
<220> FEATURE:
<221> NAME/KEY: modified_base
<222> LOCATION: (47)..(47)
<223> OTHER INFORMATION: m5c
<220> FEATURE:
<221> NAME/KEY: modified_base
<222> LOCATION: (64)..(64)
<223> OTHER INFORMATION: m5c

<400> SEQUENCE: 10
gcgggaatta cagataaatt aaaactgcga ctgcgcggcg tgagctcgct gagacttcct      60
ggacggggga caggctgtgg ggtttctcag                                      90
```

DETECTING AND SORTING METHYLATED DNA USING A SYNTHETIC NANOPORE

CROSS-REFERENCE TO RELATED APPLICATIONS

This application is the U.S. national stage application under 35 U.S.C. §371 of International Application No. PCT/US2009/068726, filed Dec. 18, 2009, which claims the benefit of U.S. Provisional Patent Application 61/139,056 filed Dec. 19, 2008, each of which is hereby incorporated by reference to the extent not inconsistent the disclosure presented herein.

STATEMENT REGARDING FEDERALLY SPONSORED RESEARCH OR DEVELOPMENT

This invention was made with government support under RO1 HG003713A awarded by the National Institute of Health. The government has certain rights in the invention.

REFERENCE TO A TABLE OF SEQUENCE LISTINGS

A sequence listing containing SEQ ID NOs:1-10 is submitted herewith and is specifically incorporated by reference. The table of sequence listings is specifically incorporated as part of the specification herein.

BACKGROUND OF THE INVENTION

Some of the cytosine residues in all vertebrate genomes are methylated, producing what amounts to a fifth DNA base, 5-methylcytosine. Methylation has been shown to regulate gene expression, and hence alter cellular state. Differentiation and development of genetically identical cells seems to be controlled by a combination of signaling and epigenetic effects, including DNA methylation state. In addition, several types of disease have shown a direct dependence on methylated state, e.g. colorectal or breast cancer. The relevance of DNA methylation in disease state, cellular control, growth and differentiation illustrates the importance of techniques capable of measuring or detecting DNA methylation.

In particular, techniques are needed to detect methylated DNA within mixtures of DNA including DNA having different methylation levels or no methylation. For example, sorting and isolating methylated DNA facilitates further analysis of DNA sequence, methylation pattern or content, including determining which regions are methylated (e.g., islands of hypermethylation) and/or unmethylated (e.g., regions of hypomethylation). Thus, techniques that can reliably, efficiently and sensitively detect, measure, classify, or separate DNA based on DNA methylation have application in a number of fields, including but not limited to health, medicine, animal and plant husbandry. Methods provided herein have use in other fields, including for example, targeting drugs, screens or assays for diseases, disease states and predisposition toward a disease.

Conventional processes known in the art separate methylated from unmethylated DNA either through immunoprecipitation of methylated DNA (MeDIP), methylation specific binding protein columns, or methylation-sensitive restriction digestion. Immunoprecipitation suffers from a lack of specificity, in that unmethylated fragments are often co-precipitated with the methylated fragments, causing those techniques to only be sensitive to large changes in methylation, restricting the technique to examining highly methylated regions. A similar problem occurs with methylation binding protein columns, as unmethylated fragments are often bound as well, and the strength of binding may vary depending on the degree of methylation. Dense methylation is required for strong, specific binding, causing the same type of problem as with MeDIP. Alternatively, methyl-sensitive restriction digestion requires relatively long intact DNA fragments, and is limited to CGs inside the recognition site, e.g. HpaII sites are only 8% of the human genome. Other, more promiscuous restriction enzymes such as McrBC alleviate this to a degree, but still suffer from lack of specificity, as well as the difficulty and sample loss associate with purifying the cut fragments from the uncut. Alternatively, bisulphite pyrosequencing can determine the methylation status of the DNA, but this method is difficult to apply to large regions of DNA.

A number of conventional techniques are used for the purpose of enriching methylated DNA from unmethylated DNA. They include 1) immunoprecipitation of methylated DNA; 2) digestion using methyl-sensitive enzymes; 3) methylation sensitive PCR; and 4) DNA methylation binding columns. Those methods are able to enrich the DNA for either methylated or unmethylated fractions, but cannot actually sort methylated from unmethylated DNA piece by piece. All of those methods need large amounts of DNA to be effective, and have low yield in the sorting process. Of course, direct analysis of bisulfite converted DNA is also a possibility, through either sequencing (pyrosequencing or Sanger sequencing) or microarray analysis.

Immunoprecipitation of methylated DNA is based on the simple concept of using a monoclonal antibody raised against 5-methyl-cytosine (mC). Genomic DNA extracted from cells or tissue is fragmented through sonication or shearing to yield fragments on the order of 1 kbp or smaller. One fraction of the fragmented DNA is then denatured and immunoprecipitated with the mC antibody. The DNA is washed, and the precipitated DNA recovered, presumably highly enriched for fragments which have one or more methylated cytosines. Usually, this methyl enriched DNA is then run on a microarray versus the other fraction of the original "input" DNA from the sonication. The two DNA fractions are labeled with Cy3 and Cy5 fluorescent markers using standard kits, and the results assayed on the microarray to obtain a ratio (Weber et al. 2005 Nature Genetics 37: 853-62). This technique suffers from two complementary problems: unmethylated DNA is sometimes co-precipitated with methylated; and methylated DNA must be densely methylated in order to be extracted in the first place. In fact, it has recently been shown (Irizarry et al. 2008 "Comprehensive high-throughput arrays for relative methylation (CHARM)" Genome Research), that this technique is barely able to globally distinguish between a cell line with a double knockout of DNA methyltransferase 1 and 3B (DKO sample) and the HCT116 cell line, a hypermethylated colorectal cancer cell line.

Methyl-sensitive digestion is another method to sort methylated from unmethylated parts from the genome. Restriction enzymes are sequence specific, and some are sensitive to whether the DNA is methylated or not. One example is HpaII and MspI, a pair of isoschizomers recognizing CCGG, with MspI insensitive to methylated status and HpaII cutting only unmethylated recognition sites. Another unique enzyme currently being used more frequently is McrBC, which recognizes any pair of $(A/G)^mCs$ that are from 40-3000 bp apart, and cuts at one of the sites (Panne et al. 1999 Journal of Molecular Biology 290(1): 49-60). Genomic DNA is first fragmented, digested with the methylation sensitive enzyme, then either amplified with recognition site specific PCR or separated by size—either way purifying the fragments which are unmethylated, with the resulting fragments separated by size. Cleavage based ligation is also possible, using primers which match the recognition site and amplify only fragments which were cut—amplifying the unmethylated fraction, as in HpaII tiny fragment Enrichment by Ligation-mediated PCR (HELP) (Khulan et al. 2006 Genome Research 16(8): 1046).

Methylation-specific PCR uses a combination of bisulfite treatment and careful primer design to determine methylation status of a given DNA locus. After bisulfite treatment, any unmethylated cytosine residue is deaminated, converting it to uracil. Methylated cytosines are protected from deamination, so they are kept as cytosines. This alters the sequence of the treated DNA in a predictable, methylation dependent way. By designing primers which amplify either unchanged cytosines or cytosines converted to uracil, the methylation status of the original genomic DNA is determined, based on which primers give product. This technique, while extremely specific and requiring relatively small amounts of genomic DNA (as few as 100 cells), does require extreme specificity—only one locus can be tested at a time for methylation, and the primer design requires specific knowledge of the area to be tested. Only one area can be tested at a time, requiring large amounts of DNA to test multiple sites, as well as long time periods and significant effort.

Separation can also be accomplished by taking advantage of the natural ability of certain DNA-binding proteins to differentiate between methylated and unmethylated DNA. By using a recombinant His-tagged version of the methyl binding domain (MBD) of MeCP2, and attaching it to a nickel-agarose matrix, a methyl sensitive stationary phase for a column is constructed (Cross et al. 1994 Nature Genetics 6(3): 236-244). Genomic DNA is then cleaved by MseI, which cuts in A/T heavy areas, yielding small CG rich fragments which may be run through the column and purified on the basis of the strength of binding. This allows for fractions to be extracted which vary in the level of methylation. The specificity of this technique is not ideal—as unmethylated DNA may also be bound by the column, and the strength of binding may vary depending on the degree of methylation. Dense methylation is needed for strong binding, essentially causing the same type of problem previously discussed with MeDIP.

Accordingly, provided herein are methods for separating DNA with high selectivity and specificity according to methylation profile and level in a relatively simple, fast and efficient manner without resorting to tags or enzymes. This is particularly advantageous in that such tags and enzymes are often expensive and difficult to implement without adversely impacting one or more of resolution, sensitivity, specificity, speed and selectivity.

BRIEF SUMMARY OF THE INVENTION

Provided herein are methods related to analyzing DNA methylation, and specifically detection, characterization and/or separation of DNA based on methylation. In particular, the methods are useful for examining a methylation parameter in a biological sample, such as the level of DNA methylation from a mixture of DNA. Disclosed herein are various methods, processes and systems that rely on the principle that there is an electric field threshold for translocation of methylated DNA through a synthetic nanopore that depends on methylation. Membranes having a nanopore with a focused and localized electric field through which a DNA molecule can translocate from a compartment adjacent to one membrane surface, through the membrane's pore, and out the opposing membrane surface adjacent a second compartment, to facilitate DNA methylation analysis, sorting and detection. Because the ability of DNA to pass, under an applied electric field, through a nanosized pore whose effective diameter is on the order of the DNA diameter or less is dependent, at least in part, on DNA methylation, systems provided herein offer a reliable, accurate and relatively simple means for analyzing DNA methylation. The methods and systems are useful in a wide range of applications, including in tests for disease state, including cancer or predisposition toward developing cancer.

In situations where a pore has a smaller diameter than the effective diameter of DNA traversing the pore, the DNA must undergo a stretching transition in order to transit the pore from one side of the pore to the other side. With larger diameter pores (>3 nm) the DNA does not need to stretch to translocate through the pore, and so does not show the same type of thresholding (although there is apparently an entropic threshold at very small voltages associated with the DNA entering the pore). The threshold voltage for stretching unmethylated DNA is known to depend on the thickness of the membrane, the conical geometry of the pore, and the surface charge in the pore. In particular, we have observed that the stretching threshold for unmethylated DNA occurs at about 3.2V in a 20 nm thick membrane, while the threshold voltage can be reduced <1V for a pore about 2.5 nm in diameter. The ability of DNA to undergo this stretching transition is also impacted in part by the presence or absence of methyl groups, including methylation of cytosine residues. In particular, methylated DNA undergoes this stretching transition at a lower threshold voltage than unmethylated DNA (for the same pore). Similarly, DNA having a specific methylation pattern will generate a unique electric potential or current profile over time as the DNA passes through the pore. These profiles permit study and separation not only based on methylation level, but also on the pattern of methylation along the DNA sequence. Because DNA is a highly charged molecule, an applied E field in the pore may be used to force DNA through the pore and differences in threshold voltage required to drive DNA through the pore used as a basis to examine or separate DNA based on methylation. In an aspect, the system and methods can be used to sieve DNA into separate components, with each component having unique methylation content.

In an embodiment, provided is a method for separating DNA based on methylation by providing a membrane having one or more nanopores, wherein the membrane separates a first compartment from a second compartment. In particular, the nanopore is in fluid communication with the first and second compartments so that DNA suspended in a fluid in a first compartment is capable, under certain conditions, of entering the pore from the first compartment and exiting the pore into the second compartment. DNA is provided to the first compartment and the DNA separated by establishing an electric field across the membrane, wherein the electric field generates a threshold voltage across the nanopore that is capable of forcing methylated DNA through the nanopore from the first to the second compartment. In an aspect, substantially no unmethylated DNA (or, more generally, DNA that does not at least meet the methylation parameter of interest does not substantially translocate via the pore) traverses the nanopore to enter the second compartment. "Substantially" refers to less than 0.1% of the unmethylated DNA (or DNA not meeting the methylation parameter of interest) passing through to the second compartment. Alternatively, the method is described in terms of DNA ratio in the second compartment. In an aspect, the number of methylated DNA fragments in the second compartment outnumbers other DNA in the second compartment by a factor that is greater than or equal to 1000.

In an aspect, any of the methods are used to separate DNA having a methylation parameter. Methylation parameter refers to any quantifiable or measureable aspect arising from the presence or absence of methyl groups on a DNA base and/or the pattern of methylation along a DNA sequence. In an aspect, the parameter is methylation level or content, methylation pattern, or methylation content/level and pattern.

The invention is optionally characterized in terms of a functional variable, such as sensitivity, resolution, selectivity, separation speed and/or accuracy. In an embodiment the method indicates the capability of separating or resolving DNA methylation for DNA differing by as little as one or two methylation site(s) per 100 bp length of DNA.

In an aspect, any of the methods provided herein may be used with any type of DNA, such as DNA from any biological or synthetic origin, ranging from genomic DNA, fragments of genomic DNA, to DNA encoding one or more genes or regulatory sequences related to gene expression, and fragments thereof. Because methylation can control gene regulation/expression or affect disease state in regions that are actually relatively far from the gene, the DNA may be selected from non-encoding regions of the genome. In an aspect, the DNA comprises a section in which methylation level is associated with alteration of cellular behavior, such as the DNA portion whose methylation level is associated with a disease state. In an aspect, the DNA is isolated then further processed, through either shearing or sonication, to generate DNA fragments having a uniform size range distribution.

Any of the methods can be used for DNA whose methylation content or pattern is associated with a disease state, such as a disease state that is cancer or that may affect the prevalence of developing a disease state. In particular, the DNA can be from a gene that is BRCA1; MS3; as well as fragments thereof, including fragments of regulatory sequences, or any of the sequences provided in TABLE 1 (SEQ ID NOs:1-10). In addition, methods provided herein are useful for screening and/or identifying genes or gene fragments in which methylation status is relevant for a biological state.

Represenative examples of others gene of interest include, but are not limited to: POU3F1, GNAL, SIM2, WIT1(Costello, Frühwald et al. 2000); PAX2—hypomethylation—endometrial cancer—(Wu, Chen et al. 2005); p16INK4A—cyclin dependent kinase inhibitor—hypermethylation—non-Hodgkin's lymphoma and melanoma—(Herman, Civin et al. 1997) (Herman, Graff et al. 1996); p15INK4B—cyclin dependent kinase inhibitor—tumor suppressor gene—hypermethylation—adult acute mylegenous leukemia and lymphocytic leukemia & pediatric acute mylegenous leukemia and lymphocytic leukemia—(Herman, Civin et al. 1997) (Herman, Graff et al. 1996); E-cadherin—hypermethylation—tumor suppressor gene—epithelial-mesenchymal transition—metastasis—esophageal, leukemia (Esteller, Corn et al. 2001); von Hippel-Lindau—hypermethylation—tumor suppressor gene—von Hippel-Lindau disease, renal tumors—angiogenesis/metastasis—(Herman, Graff et al. 1996) (Herman, Latif et al. 1994); 06-Methylguanine DNA methyltransferase (MGMT)—hypermethylation—DNA repair gene—lung, brain, gastrointestinal cancer—broad effect—(Esteller, Toyota et al. 2000; Esteller, Corn et al. 2001); BRCA1—DNA damage repair—hypermethylation—breast cancer—especially in the case of LOH of the other copy—(Esteller, Silva et al. 2000); LKB1—AKA STK11—tumor suppressor (kinase—unknown specifics)—hypermethylation—found in papillary breast carcinomas and familial hamartomous polyp lesions in families with a history of Peutz-Jeghers syndrome (syndrome which causes PJS)—(Esteller, Avizienyte et al. 2000); hMLH1—DNA mismatch repair (HNPCC)—hypermethylated—colorectal cancer—(Kane, Loda et al. 1997); S100A4—enhances metastasis—calcium-binding EF hand—colorectal—hypomethylation—(Nakamura and Takenaga 1998); Ras—important second messenger in signaling—hypomethylated—colon and lung cancer—(Feinberg and Vogelstein 1983); MAGE-1—tumor-specific antigen—hypomethylation—melanoma cancer—(Smet, Backer et al. 1996); CAGE—tumor specific antigen—hypomethylation—gastric cancer—(Cho, Lee et al. 2003); HPV-16 DNA—human papillomavirus—hypermethylated in cervical lesions—hypomethylated in asymptomatic patients—cervical cancer—(Badal, Chuang et al. 2003; De Capoa, Musolino et al. 2003); MDR1—multi-drug-resistance gene—drug efflux pump at cell membrane surface—hypomethylated—adult myeloid leukemia—(Nakayama, Wada et al. 1998); RB—Retinoblastoma gene—causes retinoblastoma—hypermethylated—(Ohtanifujita, Fujita et al. 1993); p14ARF—p53 network—hypermethylation—hematological cancers—(Esteller, Corn et al. 2001); GSTP1—metabolic enzyme—hypermethylated—breast, kidney, liver—(Esteller, Corn et al. 2001); DAPK—apoptotic gene—tumor suppressor—hypermethylated—lymphoma especially but broad—(Esteller, Corn et al. 2001); TIMP-3—metastasis associated—tissue inhibition of metallopeptidase 3—hypermethylated—kidney, brain, colon, breast, lung—everywhere, but heavily in kidney—(Bachman, Herman et al. 1999; Esteller, Corn et al. 2001); p73—cell cycle regulator—associated with p53 network—hypermethylated—blood cancers (leukemia, lymphoma)—(Esteller, Corn et al. 2001); APC—differentiation/growth—APC/b-catenin—hypermethylated—colon, but more stomach, pancreas, liver, esophagus, bladder some breast—(Esteller, Corn et al. 2001); RASSF1A—tumor suppressor gene—hypermethylated—renal and melanoma—prevents IFN mediated killing—(Reu, Leaman et al. 2006); ER—estrogen receptor—induces growth—breast cancer—hypermethylated in ⅓ of breast cancers (adding it back kills the cancer)—(Ferguson, Lapidus et al. 1995); AR—androgen receptor—induces growth—prostate cancer—hypermethylated—(Kinoshita, Shi et al. 2000); GATA-4—transcription factor—promotes differentiation—hypermethylated—colorectal—(Akiyama, Watkins et al. 2003); GATA-5—transcription factor—promotes differentiation—hypermethylated—colorectal—(Akiyama, Watkins et al. 2003); SFRPs—Wnt antagonist—promotes differentiation—hypermethylated—colorectal—(Suzuki, Watkins et al. 2004).

Although the membrane can be of any suitable material that can be processed to yield nanopores, in an aspect the membrane comprises silicon nitride ($Si_3N_4$). Similarly, the thickness of the membrane is selected as desired, depending on the DNA of interest, such as DNA length, methylation levels, or on the desired methylation parameter upon which separation is based. In an aspect, the membrane has a thickness that is selected from a range that is greater than or equal to 10 nm and less than or equal to 50 nm. Similarly, pore diameter is selected as desired. In an aspect, the pore diameter is less than or equal to the effective diameter of a DNA helix of said DNA. Alternatively, the pore diameter is selected from a range that is greater than or equal to 1.5 nm and less than or equal to 3 nm. In another embodiment, any of the methods use a pore having a diameter that is selected from a range that is greater than or equal to 1.6 nm and less than or equal to 2.5 nm. In an aspect, the membrane has a user-specified pore density selected as desired, such as ranging from a high pore density for high-throughput screens to a low density in an experiment wherein an individual DNA molecule is desirably studied. In an aspect, the membrane has a pore density selected from a range that is greater than or equal to about 1 pore/$\mu m^2$.

A density larger than this makes it difficult to electrically address each pore individually with the technology currently used to wire integrated circuits. Independent address is necessary if the pore geometry is not stringently controlled because the DNA stretching transition is exquisitely sensitive to parameters such as the cone angle of the pore, the length of the axes defining the constriction, the membrane thickness, and the surface charge on the pore. A typical choice of these parameters suitable for high throughput screening at a threshold of about 2.5-3V (for unmethylated DNA) are: cone angle, 15±5°, for a pore diameter of 2.0±0.2 nm; with a membrane thickness of 10±2 nm with a surface charge of −0.02 C/$m^2$. However, a change in the cone angle from 15±5°, such as to 20° for example, lowers the threshold by nearly a factor of 2. A change in the pore diameter to 2.5 nm changes lowers the threshold to <1V. And a change in the thickness to 20 nm would increase the threshold by a factor of 2. On the other hand, if the nanometer-scale dimensions of the pore and the surface charge are stringently controlled, then the pore density in the membrane can be increased to about 1 pore/10 $nm^2$. This density is determined by the effective diameter of the tightly-focused, high-energy electron beam currently used to sputter the pore (5-$\sigma$ of a 2 nm diameter).

In an embodiment, the electric field is selected to generate a threshold voltage across the nanopore that is capable of translocating DNA having a methylation level that is equal to or greater than a user-selected methylation level. In an aspect, the methylation level corresponds to about 5 or 6 methylated bases per sequence length of about 100 base pairs. In an aspect, the voltage applied across the membrane in conjunction with the bi-conical geometry of the pore generates a focused electric field that corresponds to a force greater than 300 pN on a single elementary electron charge. This force is well in excess of the 60 pN force required to stretch DNA.

In another aspect of the invention, any of the methods relate to selecting a threshold voltage to measure a methylation parameter, such as methylation parameter corresponding to the number of methylated sites on the DNA.

In an embodiment, any of the methods related to selecting the field strength to generate a threshold voltage across the nanopore that is greater than or equal to a user-specified field strength or voltage gradient, such as a range that is greater than or equal to 3.5V/cm, corresponding to a 60 pN force gradient applied across the bases constituting the DNA necessary to stretch the molecule.

In an aspect, the DNA is double stranded and has a length that is selected from a range that is greater than or equal to 50 base pairs and less than or equal to a length of genomic DNA, or a length selected from a range that is greater than or equal to 50 base pairs and less than or equal to 1 kbp.

In an embodiment, the invention further provides for analyzing at least a portion of DNA from the second compartment. For example, the analyzing may provide information about the sequence of DNA that translocated through the pore, or the number of DNA molecules in the second compartment. In an aspect, the analyzing step comprises DNA quantification by polymerase chain reaction, such as qPCR, or through hybridization to a DNA microarray.

In an aspect, any of the methods further comprise sequentially changing the electric field over a plurality of the separating steps to obtain a plurality of individually separated DNA, wherein each separated DNA has a methylation pattern or content different from any other separated DNA. This aspect provides for sieving of DNA based on methylation pattern or content, such as consecutively binning DNA having a high methylation content to DNA having lower methylation content, by applying consecutively higher threshold voltages across the membrane or nanopore. For example, such a sequentially changing step can be used to separate the provided DNA based on methylation content or level, wherein the provided DNA is a mixture of unmethylated, hemimethylated and methylated DNA. "Hemimethylated" refers to methylation state that is between unmethylated DNA and maximum methylation for a given DNA sequence of interest.

In another aspect, the invention provides methods of detecting DNA methylation content or methylation pattern from DNA obtained from a subject. In this aspect, a DNA sample is obtained from a subject. A membrane is provided having one or more nanopores, wherein the membrane separates a first compartment from a second compartment and the nanopore is in fluid communication with the first and second compartments. The DNA sample is provided to the first compartment and an electric field established across the membrane. The electric field generates a threshold voltage across the nanopore that is capable of forcing DNA having the methylation content or methylation pattern through the nanopore, from the first to the second compartment, and wherein substantially no DNA having the methylation content or pattern of interest traverses the nanopore to enter the second compartment (e.g., less than 1%, less than 0.1%, or less than 0.01% translocation through the pore), or the number of DNA in the second compartment outnumbers other DNA in the second compartment by a factor that is greater than or equal to 1000. The methylation content or pattern is detected by the passage of the methylated level or pattern through the membrane (e.g., real-time detection) or by detecting the presence of the methylated level or pattern of DNA in the second compartment.

In an aspect, the electric field is constant over time. Alternatively, the electric field varies over time, thereby facilitating DNA selection based on DNA pattern rather than on DNA content only.

In an embodiment, any of the methods provided herein further comprise determining a methylation content or level of the DNA by selecting the electric field to force the DNA having the methylation content or level or greater through the nanopore.

In any of the methods the DNA comprises at least a portion of a gene or a regulatory sequence thereof, wherein the portion's methylation content, level or pattern is associated with a disease state, such as cancer. In an aspect, any of the methods use DNA from a mammal, a plant or an insect. In an aspect, the mammal is a human.

Further provided are kits for determining an epigenetic state from a DNA sample. In its simplest form the kit comprises instructions for setting electric field or threshold voltage that is matched to a DNA sequence for which a methylation parameter is desired to be detected. In an embodiment, the kit has a membrane comprising a nanopore, or a plurality of nanopores. Optionally, an electrolyte solution is provided, or directions for making an electrolyte solution, that is to be applied in electrical contact with the membrane. Instructions are provided for applying an electric field across the membrane by electrically contacting the electrolyte solutions on either side of the membrane, to establish a threshold potential field across the nanopore that depends on the disease state. Optionally, the kit may contain positive controls, corresponding to DNA having the methylation parameter of interest and/or negative controls, to ensure the system is properly functioning.

In an aspect, the kit is for detecting an epigenetic state that is a cancer risk factor. In an aspect, the DNA sequence is from a human. In an aspect, the DNA is genomic DNA.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION OF THE INVENTION

Figure 1:
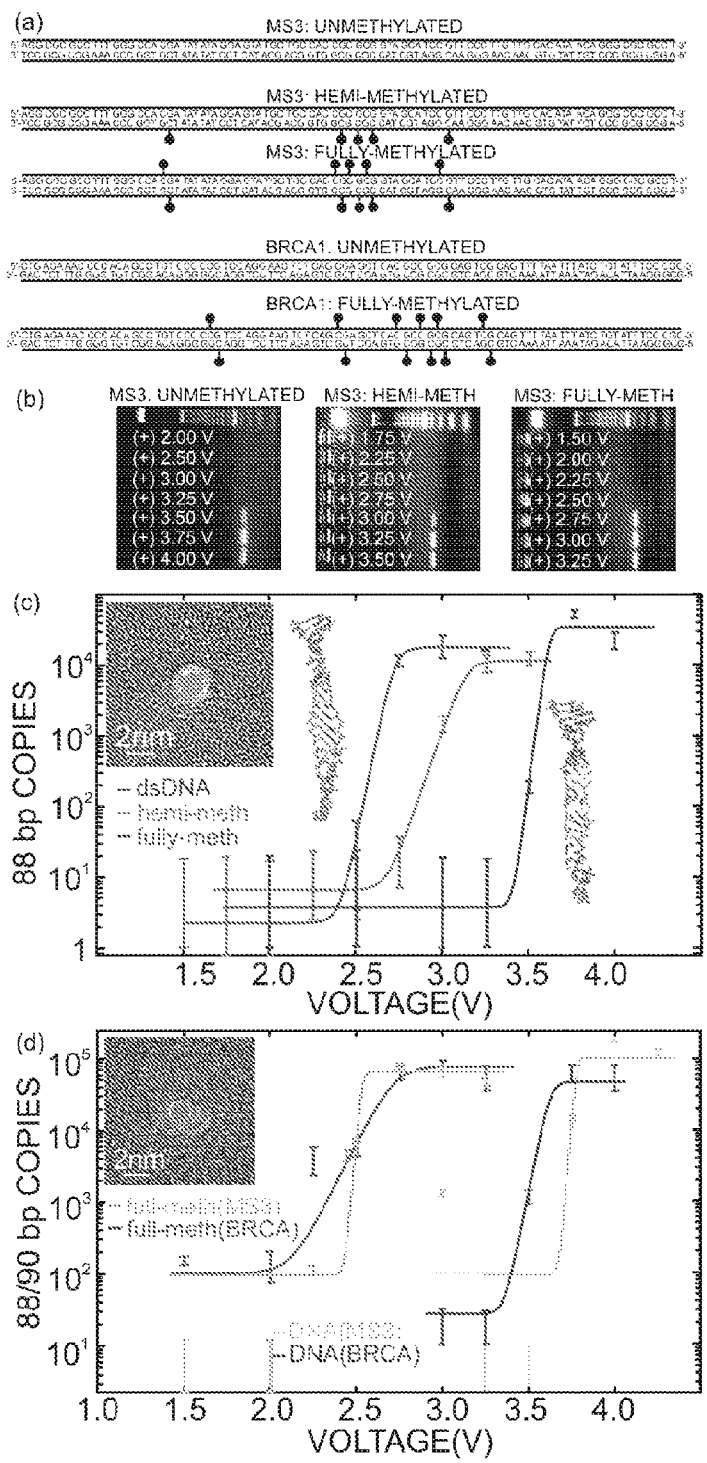
FIG. 1: The threshold voltage for DNA permeation through a synthetic nanopore depends on methylation. (a) Methylation patterns in MS3 and BRCA1 (see TABLE 1 for sequence information). The methylated CpG cites on each strand are attached to solid circles. (b) Gel electrophoresis arrays with 8 horizontal lanes indicating MS3 found at the positive (+) electrode in the trans compartment of a bi-cell with a $Si_3N_4$ membrane containing a 1.8 nm pore (see c) separating the two chambers. A 25 bp ladder in the top lane is used for gel calibration. Below that, the voltage bias across the membrane identifies the lane. Unmethylated, hemi-methylated and fully-methylated MS3 permeate the pore for voltages V>3.25 (left panel), V>2.75V (middle panel) and V>2.5V (right panel) respectively. (c) qPCR results indicating the number of MS3 DNA copies that permeate through the 1.8±0.2 nm pore shown in the inset (left) as a function of the membrane voltage. The solid lines represent a fit to the data. In agreement with the gels, unmethylated, hemi-methylated and fully-methylated MS3 permeate the 1.8 nm pore above a threshold of U>3.56V, U=3.18V, and U=2.73V, respectively. Inset middle and right are snapshots of methylated and unmethylated MS3 translocating through the 1.8 nm pore. Both DNA exhibit an ordered B-DNA form, but there is a significant degree of disorder for unmethylated DNA. The highlighted region of the strand shows the portion of the DNA where methylated cytosines are located. The same region is also highlighted in the unmethylated strand for comparison. (d) qPCR results indicating the number of MS3 and BRCA1 DNA copies that permeate through the 1.7±0.2 nm pore shown in the inset as a function of the membrane voltage. The solid lines represent a fit to the data Unmethylated MS3 and BRCA1 permeate the V>3.77V and V=3.61V, respectively while the threshold for fully methylated MS3 and BRCA1 are V>2.53V and V=2.69V respectively.

Disclosed herein are various methods that are based on the recognition that methylation stiffens DNA and that an electric field stretches methylated DNA differently than unmethylated DNA. Accordingly, provided herein are methods and processes for detecting DNA methylation by examining DNA response to an applied electric field localized in a confined region, such as an applied electric field to DNA introduced to a nanopore in a membrane. "Methylation" refers to DNA having one or more residues that are methylated. For example, in all vertebrate genomes some of the cytosine residues are methylated. DNA methylation can affect gene expression and, for some genes, is an epigenetic marker for cancer. Two different aspects of DNA methylation can be important: methylation level or content as well as the pattern of methylation. "Methylation parameter" is used broadly herein to refer to any aspect of methylation that is of interest from the standpoint of epigenetics, disease state, or DNA status and includes methylation content, distribution, pattern, density, and spatial variations thereof along the DNA sequence. In addition, methylation parameter refers to a quantitative variable that is affected by methylation, such as for example, translocation speed through a nanopore, or variations in the electric field (e.g., changes in ionic current) in the nanopore as DNA enters and transits the pore.

"Separating DNA" refers to sorting of heterogeneous mixture of DNA molecules having a different methylation parameter, including but not limited to, methylation level, content and/or pattern. In an aspect, the separation is separating methylated DNA from unmethylated DNA. In an aspect, methylated DNA may be further separated based on methylation level or methylation pattern.

"Methylation content" or "methylation level" refers to the total number of methylated residues, such as the total number of methylated sites on the DNA of interest, such as a gene or a relevant fragment of a gene. In particular, "methylation content" is a measure of the total fraction of nucleotide residues (e.g., cytosines) that are methylated. "Methylation level" refers to the average methylation occupancy at a particular cytosine residue.

"Methylation pattern" or "pattern of methylation" refers to the distribution and location of methylated sites on the DNA of interest. In an aspect, the DNA is single stranded. For example, gene expression may be affected even for when the methylation content does not change in situations where methylated regions or sites change or shift to different locations along the strand. In an aspect, aberrant hypermethylation or hypomethylation in one or more regions results in change in expression of a relevant protein and can be a factor leading to cancer. A "methylation level profile" refers to measurement of DNA methylation at multiple dinucleotide (e.g., C-G) sites throughout the genome. Although global genomic DNA methylation content may have a role in carcinogenesis, its measurement in a cancer cell may have little to offer as a molecular marker. On the other hand, methylation levels at individual CpG dinulceotides can be useful for quantifying differences at regulatory sequences, and thereby provide methods or assays for a disease state.

"Membrane" refers to a material that is capable of preventing passage of DNA through its bulk phase under an applied electric field, except through one or more pores that traverse from one face of the membrane to the opposing face. A membrane that is placed in a fluid is capable of separating the fluid into two compartments, with one compartment adjacent to a first membrane surface and a second compartment adjacent to a second membrane surface that is opposed to the first membrane surface. Similarly, the membrane can separate two compartments, where each compartment has a different fluid composition, such as electrolyte concentration, for example.

Two compartments separated by a membrane are said to be in "fluid communication" with each other if DNA suspended in the electrolyte liquid is capable of moving between compartments via the nanopore, including movement under an applied electric field.

"Pore" refers to a passage through the membrane that, without an applied electric field threshold, does not permit passage of DNA, such as linear DNA. Depending on the experimental set-up, the pore may be a nanopore having an effective diameter that prevents passage of DNA unless a suitable electric potential is applied across the entrance and exit of the nanopore. In an aspect, the nanopore is generally cylindrical in shape. In an aspect, the nanopore has at least a portion that is tapered, such as having a maximum diameter on the surface, and a minimum diameter at a position that is at a vertical location in the membrane. For example, the minimum diameter may be equidistant from the membrane first surface and second surface. One example of a pore geometry are bisecting cones illustrated in FIG. 3C. In one embodiment, "pore diameter" refers to the minimum diameter for a pore whose cross-sectional area varies with membrane vertical location.

"Threshold voltage" refers to the voltage required for DNA to permeate through a nanopore, such as a synthetic nanopore in a membrane. In particular, for nanopore diameters that are smaller than the diameter of the DNA, the DNA undergoes a stretching transition that depends on pore geometry, methylation level, and methylation pattern. Accordingly, for a given pore geometry and composition, the threshold voltage depends on DNA methylation, and can, for example, differ by as much as 1 V (for a 20 nm thick membrane) for different methylation levels. Variation in threshold voltage with methylation level provides a useful basis for discriminating methylated from unmethylated DNA, distinguishing between methylation levels, and detecting different methylation patterns. In an aspect, threshold voltage is defined relative to the ratio of the number of methylated to unmethylated DNA (or, more generally, DNA of interest having a methylation parameter of interest compared to DNA where the methylation parameter is less than that or different from the methylation parameter of interest) that pass from a first compartment to a second compartment via the nanopore. In an aspect, the ratio is at least 100:1, at least 1000:1, or at least 10,000:1. Alternatively, threshold voltage can be functionally described in terms of the amount of unwanted DNA (e.g., not meeting the methylation parameter of interest) that passes through to the second compartment. In an aspect, the threshold voltage results in less than 1%, less than 0.1%, or less than 0.01% of DNA not meeting or satisfying the methylation parameter of interest passing through to the second compartment.

The efficacy of an assay is ultimately determined by its sensitivity and specificity. Absolute sensitivity refers to the minimal quantity of a pure methylated target DNA that the assay is able to detect. Provided herein are methods having a sensitivity sufficient to distinguish, detect, or sort between DNA that differ by as little as 1 or 2 methylation sites over 100 bp. Provided herein are methods having a specificity that is capable of detecting DNA having a user-selected methylation parameter from a mixture of DNA, wherein the ratio of the number of DNA molecules having the methylation parameter of interest to the number of DNA molecules not having the methylation parameter of interest is selected from a range that is between 1:100 and 1:100,000. "Resolution" refers to the ability to sort DNA from other DNA having a different methylation parameter. In an embodiment, resolution is expressed in terms of a percentage difference in methylation content, such as a resolution capable of sorting or detecting DNA whose methylation content differs by 20% or greater. Similarly, the resolution may be expressed in terms of detecting or sorting based on a methylation parameter that is methylation pattern.

"Disease state" refers to a detection of a methylation parameter of DNA that is related to a disease or a predisposition for developing a disease. For example, particular types of cancer are related to methylation state, such as change in methylation content and/or pattern such as for genes that are involved in tumor suppression, for example. Similarly, certain cancer cells have unique methylation parameters such as content or pattern, for example. Accordingly, various methods provided herein may be used to detect the disease state of cancer or may be used to predict an individual's susceptibility for developing cancer, facilitating remedial action or more in depth cancer monitoring.

"Effective diameter" refers to an average diameter of linear DNA without application of an electric field. Accordingly, a pore diameter less than the DNA effective diameter refers to the pore through which DNA cannot transit without undergoing a stretching-transition that effectively decreases the DNA diameter.

"Sequentially changing" refers to sequential steps of separating or sorting DNA based on methylation. For example, in aspects where more than simple methylated or unmethylated separation is desired, the method may be run as a sequential sieve, that in separate steps separates DNA by varying the electric field in a number of steps. This can separate DNA based on methylation content, ranging initially from high methylation content (e.g., lower threshold voltage), to an intermediate content (intermediate threshold voltage) to low or no methylation (higher threshold voltage).

"DNA sample" may be any material obtained from a subject that provides DNA of interest, including genomic DNA, at least a portion of the DNA genome, a fragment of the DNA genome containing a contiguous sequence of DNA, such as a portion of a gene of interest, including DNA sequence that is part of a regulatory sequence. "Subject" is used broadly to refer to any individual having DNA for which one or more methylation parameters are of interest. In an aspect, the subject is a mammal, a human, a plant, fungi or bacteria.

"Detecting" is used broadly to refer to a technique that, directly or indirectly, provides information about DNA methylation or a DNA methylation parameter. For example, DNA content and/or pattern may be detected based on high speed measurements of pore current during permeation of DNA through the pore. Alternatively, the number of molecules permeating the membrane through the pore can be determined by analyzing the DNA that has permeated through the nanopore, such as by qPCR.

An electric field that is "constant over time" refers to the threshold voltage across the nanopore that does not change with time, such as by deviating less than 5% from an average value. In contrast, an electric field that varies over time is optionally used to vary the voltage threshold during DNA translocation through the pore, such as to either trap the DNA molecule in the pore or to favor transit of DNA having a specific methylation pattern only.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Example 1

Nanoelectromechanics of Methylated DNA in a Synthetic Nanopore

Methylation of cytosine is a covalent modification of DNA that can be used to silence genes, orchestrating a myriad of biological processes including cancer. We have discovered that a synthetic nanopore in a membrane comparable in thickness to a protein binding site can be used to detect methylation. We observe a voltage threshold for permeation of methylated DNA through a <2 nm diameter pore, which we attribute to the stretching transition, that can differ by >1V/20 nm depending on the methylation level, but not the DNA sequence.

Some of the cytosine residues in all vertebrate genomes are methylated, producing what amounts to a fifth DNA base, 5-methylcytosine(1). Methylation adds information not encoded in the DNA sequence, but it does not interfere with the Watson-Crick pairing—the methyl group is positioned in the major groove of the DNA. The pattern of methylation controls protein binding to target sites on DNA, affecting changes in gene expression and in chromatin organization, often silencing genes, which physiologically orchestrates processes like differentiation, and pathologically leads to cancer(1). While DNA methylation has a profound effect on biological functions by inhibiting protein binding, the actual mechanism that inhibits binding is still mysterious. The structure of methylated DNA inferred from x-ray diffraction and NMR indicates that the effect of methylation on the conformation of DNA is very subtle, and localized near the methylation site(2). On the other hand, the DNA dynamics at the methylation site seems to be dramatically reduced—i.e. the molecule gets stiffer(3). Molecular Dynamics (MD) simulations indicate that the methyl groups reduce the DNA flexibility because of the steric hindrance (the methyl groups are bulky) and because the DNA folds around it (they're also hydrophobic).

The prospects of using DNA methylation as a molecular diagnostic in medicine are stymied by limitations of the technology used for detection. Immunoprecipitation of methylated DNA or methylation-sensitive restriction digestion represent the state-of-the-art for discriminating methylated from unmethylated DNA. Immunoprecipitation suffers a lack of sensitivity, causing the technique to only be sensitive to large changes in methylation. Methyl-sensitive restriction digestion requires relatively long intact DNA fragments and is limited to CpGs in recognition sites.

Here, we report measurements of the permeation of methylated DNA through a synthetic nanopore, using an electric field to force single molecules to translocate across the membrane through the pore. The diameter of the pore is so small that molecules can only move through it one at a time, while the thin membrane (~20 nm) offers the opportunity to test the electromechanical properties of methylated DNA on size comparable to a protein-binding site (3-10 nm). In this example, for pores <2.0 nm in diameter—smaller than the DNA helix—we find a voltage threshold for permeation of DNA that depends on the methylation level.

We study two fragments of genomic DNA that are known to control expression based on methylation status: MS3 and BRCA1 (see TABLE 1). MS3 is one of the CTCF binding sites of the IGF2 imprinting control region (ICR)(4). Methylation of MS3 prevents CTCF binding, allowing an enhancer to reach IGF2 and turn on expression. Aberrant hypermethylation causes elevated expression of IGF2, which has been shown to encourage cancer. In contrast, BRCA1 is a tumor suppressor gene used to repair DNA. Methylation of the BRCA1 promoter causes binding of a protein (MeCP2) that inhibits expression leading to mutations and breast/ovarian cancer(5).

The fabrication of synthetic nanopores in $Si_3N_4$ membranes has been described in detail elsewhere(6). The insets to FIGS. 1 (c,d) show transmission electron micrographs (TEMs) taken at a tilt angle of 0°, of roughly circular pores with apparent diameters of d=1.8±0.2 nm and 1.7±0.2 nm in membranes 22±3 nm and 17±3 nm thick respectively. Using images taken at different tilt angles, we model the pore geometry as two intersecting cones each with >10° cone angle(6). We characterized electrolytic conductance for each pore, a line fit to the data yields 553±6 pS and 470±9 pS for the pores shown in the insets to FIGS. 1 (c) and (d) respectively. Next, we test the electric field driven permeability of DNA through the pore. The bi-cell used for the transport experiments is filled with 100 mM KCl electrolytic solution, buffered to pH~8 with 10 mM Tris-HCl. We then inject a concentration of $10^9$ molecules/μL into the cathode chamber of the bi-cell, apply a voltage across the membrane using Ag/AgCl electrodes, and monitor the current through the pore for 3 h. We have previously reported that voltage-driven translocations of the DNA cause a temporary blockade of the open pore current (7). However, for the electric fields used in these experiments the translocation velocity is supposed to >1 bp/μs(8). The membrane capacitance (>100 pF) precludes observation of transients shorter than 10-100 μs because the displacement current through the membrane predominates over the pore current. So, to unambiguously establish that the DNA injected at the cathode permeates a pore, we assay the sample from the anode using either PCR amplification followed by agarose gel electrophoresis (AGE) or real-time quantitative polymerase chain reaction (qPCR) as described in detail elsewhere(7). For AGE, the DNA is first concentrated and then amplified with a kit from Invitrogen (Carlsbad, Calif.) using primers from IDT (Coralville, Iowa), finally run on an agarose gel. Alternatively, concentrated anode DNA is analyzed by qPCR using the SYBR Green kit (Invitrogen). qPCR is used prevalently as the standard for DNA quantitation and is considered highly reliable(9).

We investigate the permeability of MS3 and BRCA1 with different methylation levels and profiles through two pores with similar (1.8 nm) diameters. The patterns of methylated CpG sites in the five strands used here are shown in FIG. 1(a) (with sequences appended in Table 1). The gel arrays shown in FIG. 1(b) illustrate permeability of the 1.8 nm pore shown in the inset to (c) as a function of the voltage applied across the membrane. The left gel indicates a threshold voltage for permeation of unmethylated DNA is V>3.25 V. We have previously reported similar phenomena and used molecular dynamics (MD) to interpret the threshold as evidence of the stretching transition in DNA(7). The electric force on the DNA in a synthetic nanopore drops abruptly away from the center of the membrane, $z_0$, according to: $F(z) \sim (bV/\pi L_{mem}) \times 1/(1+(b(z-z_0)/L_{mem})^2$, where $L_{mem}$ denotes the membrane thickness, $z-z_0$ represents the distance from the center of the membrane along the axis of the pore, V denotes the applied voltage bias across the membrane and b is a geometric factor (7). At low voltage, the DNA penetrates the bi-conical pore to a diameter of about 2.5 nm, where the translocation stalls. At threshold, the differential force acting on the leading nucleotides is sufficient (~60 pN) to stretch the helix towards the center of the membrane. As it stretches, the force on the leading edge increases pulling the DNA through the pore.

The other gel arrays shown in (b) indicate that the same pore can be used to discriminate fully methylated and hemi-methylated from unmethylated DNA. Notice that the threshold voltages for permeation of fully- and hemi-methylated DNA through the 1.8 nm pores is V>2.5 V and V>2.75 V, respectively—both smaller than the threshold for unmethylated DNA. The voltage thresholds inferred from these gels are corroborated by separate qPCR experiments on the same pore. FIG. 1(c) represents the results of three qPCR analyses—one for unmethylated, one for hemi- and another for fully methylated DNA—showing the number of DNA copies translocating through the pore as a function of the applied potential.

Generally, we observe that the amount of DNA that permeates the pore rises abruptly over a range of ~250 mV near a threshold that is especially sensitive to the DNA methylation level. The permeation rate can essentially be described by the transition-state relation of the Kramers type: $R=R_0(q^*V-U)/(1-\exp[(q^*V-U)/kT])$, where $R_0$ is a frequency factor, U is the barrier height, $q^*V$ is the reduction in the energy barrier due to the applied potential, and kT represents the thermal energy(10). Using these relations and accounting for the qPCR baseline, the data was fit; the results overlay the scatter plots in FIG. 1.

The threshold voltages for fully- and hemi-methylated MS3 are consistently below that observed for the unmethylated strand and therefore, are easily resolved. For example, the threshold for unmethylated MS3 in FIG. 1(c) is about 3.61 V while hemi- and fully-methylated MS3 show a threshold of 3.11 V and 2.73 V respectively. The change in threshold is also consistent with features observed in MD simulations of the translocation of DNA strands. Snapshots of the DNA in the pore shown in (c) reveal the molecular structure with atomic detail, indicating that both methylated and unmethylated DNA exhibit a B-form, but methylated DNA is more ordered. The preservation of the B-form in methylated DNA is also evident in the root-mean-square (RMS) deviation in the helix diameter. At 4 V, the interior segments of methylated and unmethylated DNA have an RMS deviation 0.29 nm and 0.49 nm, respectively. Correspondingly, the translocation velocity of the methylated MS3 through the pore at 4V is higher (1.0 nm/ns) and than unmethylated (0.8 nm/ns).

Though the threshold is apparently related to the methylation level, it is relatively insensitive to the DNA sequence, as evident from the comparison between the permeation of MS3 and BRCA1 through a 1.7±0.2 nm pore shown in (d). The BRCA1 and MS3 sequences are different, but the thresholds for stretching the unmethylated forms are similar: 3.61 V and 3.77 V respectively. Yet fully methylated BRCA1, which has 12 methylated CpG sites and fully methylated MS3, which has a comparable number (10), both show a similar shift in threshold to 2.69 V and 2.53 V respectively. The large shifts in the thresholds with methylation (which appear to be only weakly dependent on sequence) are surprising because the leading nucleotides in the strand are separated by a distance >18 bp (~6 nm) from any methylation site, which is comparable to the length of a protein binding site.

This example demonstrates a sensitive means to detect the covalent modification of DNA by methylation, such as by methylation of cytosines, by measuring the change in the electromechanical properties of the DNA strand. For example full methylation at a single CpG site shifts the threshold by about 100 mV relative to unmethylated DNA, while full methylation shifts the threshold by greater than 0.75 V, while the change in DNA sequence (compare MS3 to BRCA) does not significantly affect threshold beyond differences that can be attributed to the change in the number of methylation sites (e.g., from 5 to 6). Due to the biconical nature of the pore, the electric field is focused near the central 4 nm of the membrane, which is comparable to a protein binding site. How proteins specifically recognize methylation is still controversial, but proteins like the methyl binding protein MeCP2 must encounter DNA electromechanics similar to that seen in these synthetic pores. Based on gel mobility shift assays, the effect of methylation is supposed to be local to the methylation site(11), but our data indicates that the effect of methylation affects the electromechanics of the leading edge of a DNA strand at least 18 bp away. Thus, methylation markers may affect protein binding to DNA on the same scale. This technology can be used as a sieving technique, to separate DNA based on methylation. Potential applications for this separation methodology include, but are not limited to, epigenetic analysis, replacing existing technologies such as MeDIP or HELP.

REFERENCES FOR EXAMPLE 1

1. Brena, R. M., T. H. M. Huang, and C. Plass. 2006. Toward a human epigenome. Nature Genetics 38:1359-1360.
2. Heinemann, U. and M. Hahn. 1992. CCAGGC-m5C-TGG. Helical fine structure, hydration, and comparison with CCAGGCCTGG. Journal of Biological Chemistry 267:7332-7341.
3. Nathan, D. and D. M. Crothers. 2002. Bending and flexibility of methylated and unmethylated EcoRI DNA. Journal of Molecular Biology 316:7-17.
4. Bell, A. C. and G. Felsenfeld. 2000. Methylation of a CTCF-dependent boundary controls imprinted expression of the Igf2 gene. Nature 405:482-485.
5. Catteau, A. and J. R. Morris. 2002. BRCA1 methylation: a significant role in tumour development? Seminars in Cancer Biology 12:359-371.
6. Ho, C., R. Qiao, J. B. Heng, A. Chatterjee, R. J. Timp, N. R. Aluru, and G. Timp. 2005. Electrolytic transport through a synthetic nanometer-diameter pore. Proceedings of the National Academy of Sciences 102:10445.
7. Heng, J. B., A. Aksimentiev, C. Ho, P. Marks, Y. V. Grinkova, S. Sligar, K. Schulten, and G. Timp. 2006. The Electromechanics of DNA in a Synthetic Nanopore. Biophysical Journal 90:1098-1106.
8. Aksimentiev, A., J. B. Heng, G. Timp, and K. Schulten. 2004. Microscopic Kinetics of DNA Translocation through Synthetic Nanopores. Biophysical Journal 87:2086-2097.
9. Bookout, A. L., C. L. Cummins, D. J. Mangelsdorf, J. M. Pesola, and M. F. Kramer. 2006. High-throughput real- 10. Goychuk, I. and P. Hanggi. 2002. Ion channel gating: A first-passage time analysis of the Kramers type. Proceedings of the National Academy of Sciences 99:3552.
11. Fraga, M. F., E. Ballestar, G. Montoya, P. Taysavang, P. A. Wade, and M. Esteller. 2003. The affinity of different MBD proteins for a specific methylated locus depends on their intrinsic binding properties. Nucleic Acids Research 31:1765.

Figure 2:
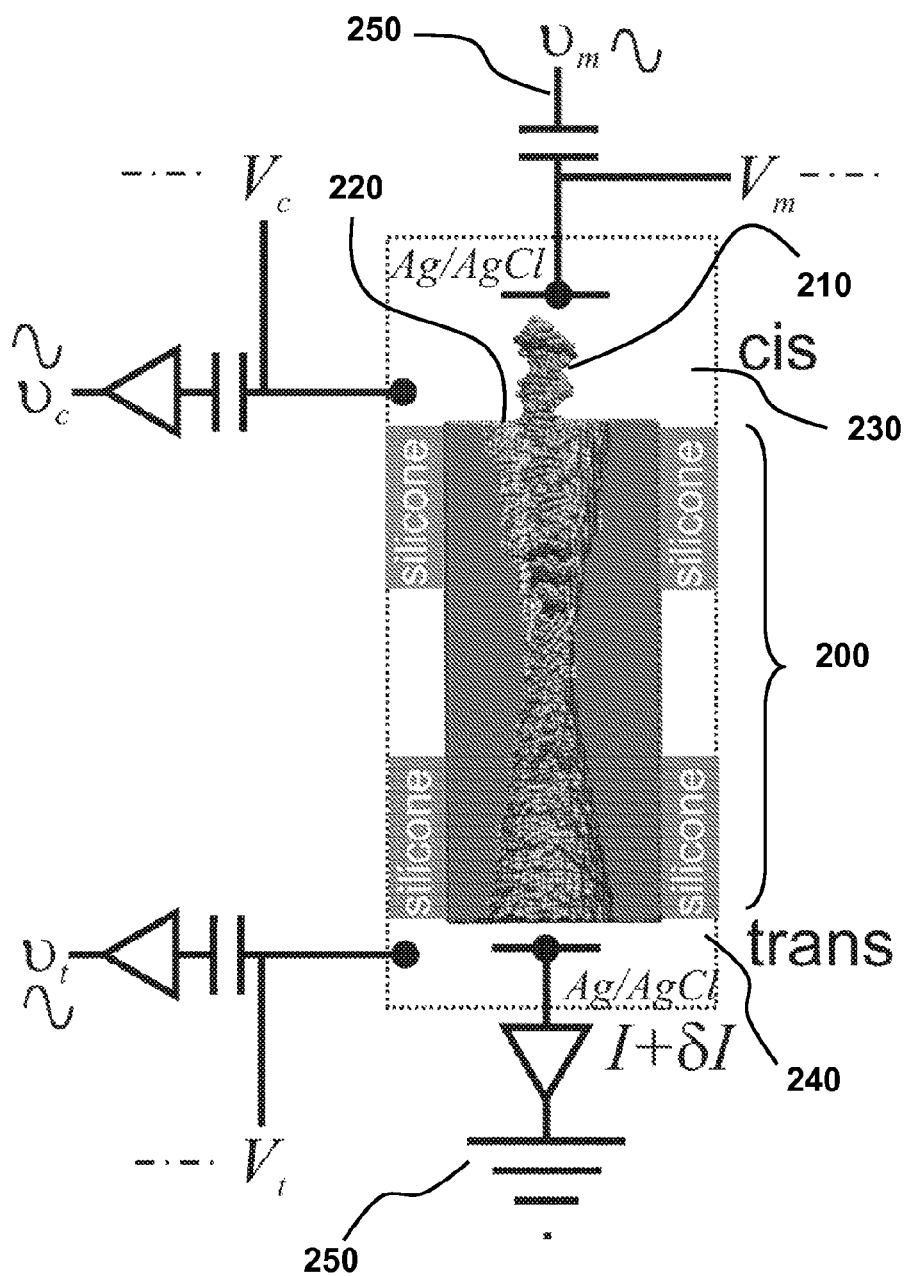
FIG. 2: A nanopore sensor for profiling methylated DNA. The figure shows methylated DNA translocating through a 1.8 nm diameter pore in a membrane formed from a silicon nitride. 5-methylcytosine are highlighted. The voltage $V_m$ drives the molecule through the pore, and can be used to arrest the translocation. The molecular configuration is probed by measurements of the blockade current δI and the AC voltages induced on the electrodes $v_t$ and $v_c$ by the drive $v_m$.

FIG. 2 is one example of a nanopore system for sorting, separating or otherwise detecting methylated DNA. A silicon nitride membrane 200 has a pore 220 through which DNA 210 is capable of permeating under an electric field applied across a first compartment 230 and second compartment 240 by electrodes 250. FIG. 2 also illustrates additional optional elements related to feedback control and low-noise, high frequency, lock-in detection to trap individual DNA molecules (such as methylated DNA) and to measure the electrical signal that develops as it is forced to permeate through the pore 220. Such systems are capable of analyzing individual DNA molecules. The system in FIG. 2 is optionally embodied as a silicon integrated circuit that incorporates an on-chip nanopore mechanism with a molecular trap to measure the electrical signal that develops when DNA translocates through the pore. An important component is a single nanometer-diameter pore in a robust, nanometer-thick membrane, as illustrated schematically in the cross-section of FIG. 2. When an electric field is applied across a membrane with a nanopore in it, DNA immersed in electrolyte migrates from the cathode in electrical communication with first compartment 230 toward the anode in electrical communication with second compartment 240, eventually permeating the membrane by translocating through the pore one molecule at a time. The pore diameter and geometry, the thickness and composition of the membrane can all be controlled with subnanometer precision using semiconductor nanofabrication practices known in the art. This precision translates directly into control of the distribution of the electric field, which has already led to the development of the most sensitive device for charge measurement: the single electron transistor.

To discriminate methylated from unmethylated DNA, the nanopore mechanism illustrated in FIG. 2 is operated in a manner that is functionally similar to molecular tweezers, using the electric field in the pore to trap and hold the stretched molecule for lockin measurements of a current signature through the pore. Based on molecular dynamic simulations we design a trap in which DNA is forced by a large electric field to stretch and penetrate into a pore that is smaller in diameter than the double helix. Once the DNA enters the pore and the electrolytic current through it is blocked, the transmembrane bias under feedback control is reduced, stalling the translocation. The strain field holds the molecule in place against thermal fluctuations while low-noise synchronous (lock-in) measurements are performed to reveal an electrical current signature indicative of methylation. Once the measurement is accomplished, a voltage pulse is applied to induce the molecule to advance through the pore potentially one base at a time.

Figure 3:
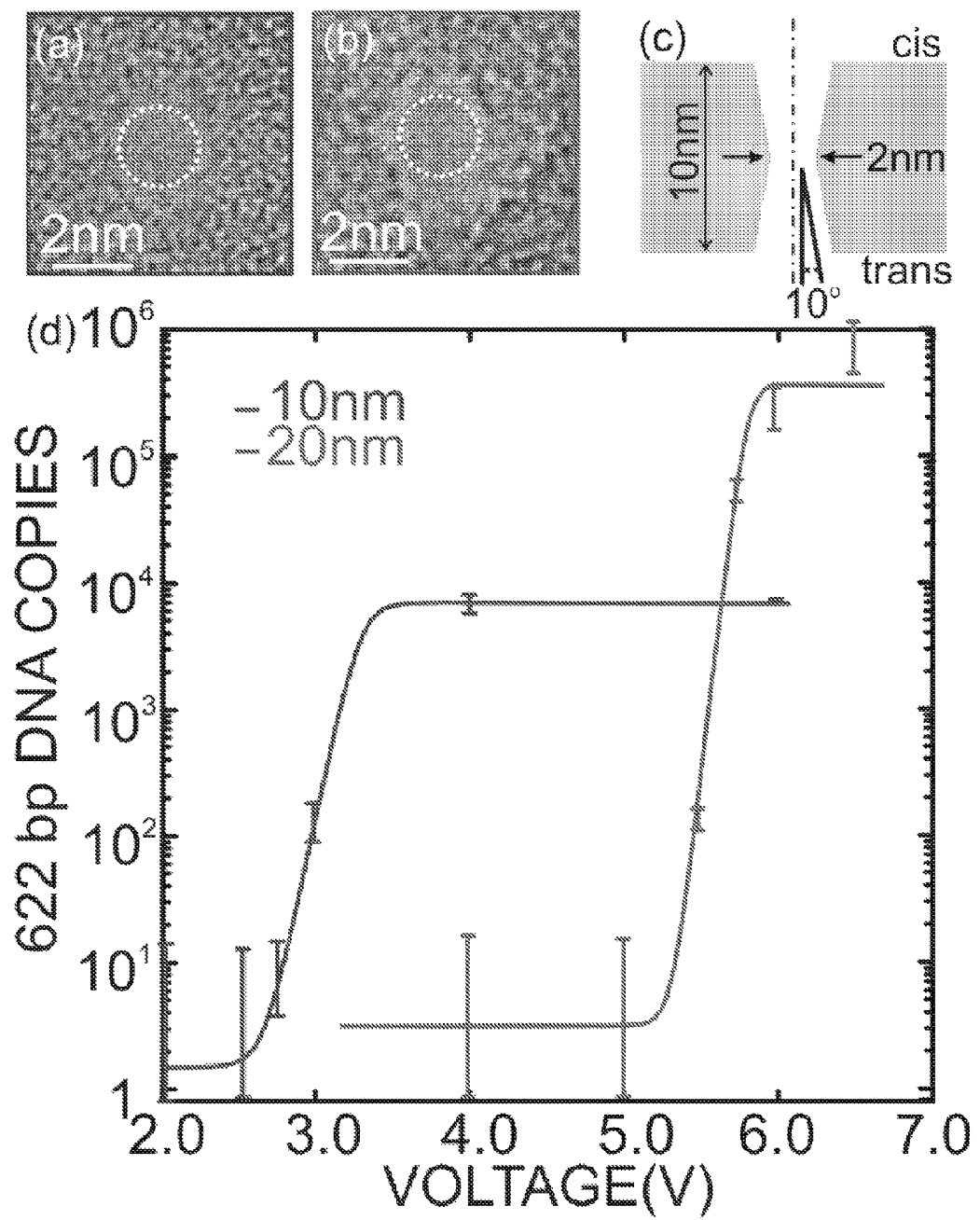
FIGS. 3 (a) and (b) TEM images of pores with apparent diameter of 2.0±0.2, in a 10 nm thick $Si_3N_4$ membrane and 1.8×2.2 nm in $Si_3N_4$ 20 nm thick membrane respectively. (c) Schematic representation of one model of the pore geometry. We find that the cone angle can range from 10° to 30°. (d) qPCR obtained for the 2 nm and 1.8×2.2 pores of figures (a, blue) and (b, red) showing the copy number versus voltage. The solid lines are fits to the data. 622 bp dsDNA permeates the 2 nm pore in a 10 nm membrane for V>2.5V, and the 1.8×2.2 $nm^2$-pore in the 20 nm membrane for V>5V.

DNA is an unusually stiff, highly charged polymer. The stiffness is due mainly to base-stacking and the double helical structure, while most of the (negative) charge is accounted for by the phosphate backbone. The electromechanical properties of DNA inferred from electric field-induced translocations through a synthetic nanometer-diameter pore in a silicon nitride membrane have been examined. This effort demanded synthetic pores comparable in diameter to DNA, ranging from 1-3 nm—the smallest synthetics ever made. The experimental procedures used to fabricate and characterize the synthetic nanopores are described herein and elsewhere (e.g., Ho et al. PNAS 102(3):10445-450 (2005)). FIGS. 3(a) and (b) are TEM images taken at a tilt angle of 0° of pores with apparent diameter of d=1.9±0.2 nm in a $Si_3N_4$ membrane nominally 10 nm thick and 1.8×2.2 nm in $Si_3N_4$ 20 nm thick. These TEM images represent two-dimensional (2D) projections through the membrane; the shot noise observed in the central area identified with the pore indicates perfect transmission of electrons. To investigate the 3D structure, we tilt the membrane in the TEM about the pore axis and explore defocus conditions. One possible pore geometry, illustrated schematically in FIG. 3(c), is represented by two intersecting cones with a cone angle ranging from 10° to 30°.

We use an electric field to force single molecules of ssDNA and dsDNA through these synthetic pores. We have shown that for low electric fields, e.g., less than 0.2 MV/cm (200 mV/10 nm), ssDNA can permeate pores with diameters $\geq 1.0$ nm, while dsDNA only permeates pores with diameters $d \geq 2.5$ nm. We also report that field-driven translocations of the ssDNA cause temporary blockades of the open current $I_0$ through the pore lasting less than milliseconds typically. The observed current transients are easily resolved from the electronic noise, but the narrow bandwidth (10 kHz) of the current amplifier coupled with the membrane capacitance precludes the observation of transients shorter than 10-100 μsec. This is especially relevant since the translocation velocity of DNA through >5 nm pores is estimated to be >1 bp/30 nsec at these voltages. Long duration current transients measured with <100 kHz bandwidth does not necessarily signal a translocation across the membrane.

To determine if a larger electric field could impel dsDNA through a pore d<2.5 nm, we tested permeability as a function of voltage using the d=2.0 nm pore in a nominally 10 nm membrane shown in FIG. 3(a), and the 1.8×2.2 nm2-cross-section pore in a 20 nm thick membrane. FIG. 3(d) represents the results of two qPCR analyses showing the number of copies permeating as a function of the potential. We use qPCR because we cannot account for all of the translocations due to the limited bandwidth of the current measurement. We find that the 2.0 nm pore in the 10 nm membrane exhibits a threshold for permeation of 622 bp dsDNA >2.5V, while the 1.8×2.2 $nm^2$ pore in the 20 nm membrane shows a threshold >5V. We attribute the change in threshold to the different thicknesses and infer that electric field causes the shift.

Figure 4:
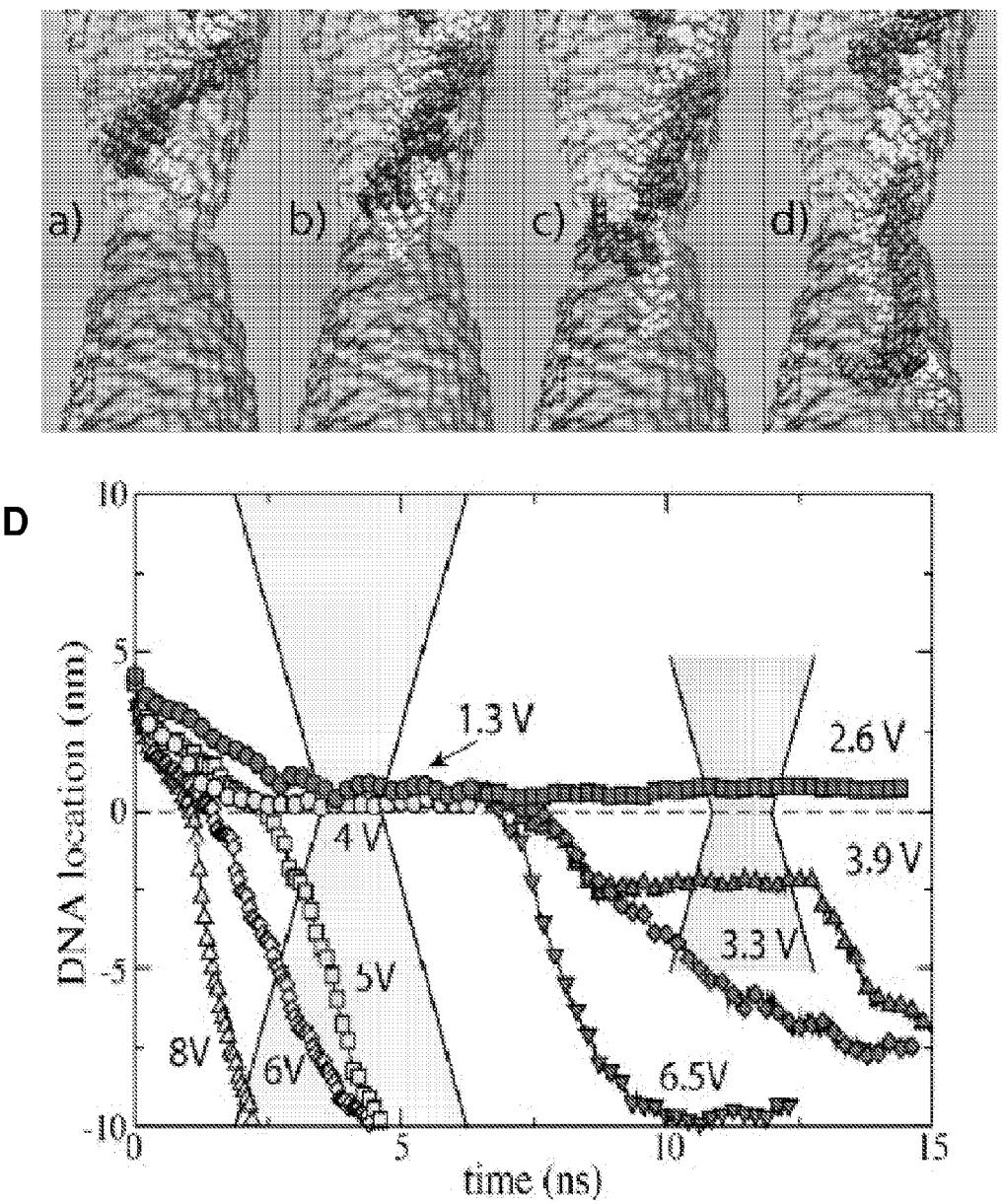
FIG. 4 Snapshots illustrating an MD simulation of a DNA translocation through a 2.0 nm pore in a 10 nm membrane driven by a 3.2V bias. (a) The helix is only slightly stretched. (b) After 1.6 ns, DNA stretches reaching the center of the membrane. (c) DNA ends fray after about 2.1 ns. (d) Both DNA ends pass through the pore constriction. D Permeation of dsDNA through 2.0-nm pores in 10 nm (blue—right side image) and 20 nm (yellow—left side image) thick $Si_3N_4$ membranes. The latter pore has an elliptic 1.8×2.2 $nm^2$ cross-section. The symbols indicate the location of the DNA leading edge as it permeates through the pore (from top to bottom). The voltage threshold for dsDNA permeation is between 2.6 and 3.2V.

To discover the microscopic origin of the field threshold, we conduct MD simulations of dsDNA translocations through 2 nm pores in both 10 and 20 nm thick membranes. FIGS. 4(a-d) illustrate a typical translocation observed at a voltage greater than threshold. When a 3.2V bias is applied, it generates a force sufficient to stretch the double helix enabling it to reach the center of the membrane. When passing by the narrowest part of the pore, the DNA ends unzip as shown in FIG. 3(c). After both strands pass through the pore constriction, FIG. 3(d), the translocation reaches a steady-state regime, in which the DNA is stretched in the middle of the pore, relaxing outside of the membrane. The pore geometry constrains the structural fluctuations destabilizing the stretched DNA conformation and so the pattern of hydrogen bonds is preserved when dsDNA permeates a 2.0 nm pore. FIG. 4D shows the position of the leading edge of the DNA relative to the center of the membrane as a function of simulation time; the symbols in the plot identify simulations carried out at different biases for the two pores. For both pores, we observe a threshold for permeation of dsDNA that agrees quantitatively with experiment.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a size or distance range, a ratio range of DNA content, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Table of sequence listings

| SEQ ID NO: | Description GENE (methyl status) | Sequence (5' to 3')—methylation of C highlighted with "$^{m5}$C" |
|---|---|---|
| 1 | MS3 (unmethyl.) Bottom strand | AGG CGC GCC TTT GGG CCA CGA TAT ATA GGA GTA TGC TGC CAC CGC GCG GTA GCA TCC GTT CCC TTG TTG CAC ATA ACA GGG CGC GCC T |
| 2 | MS3 (unmethyl.) Top strand | AGG CGC GCC CTG TTA TGT GCA ACA AGG GAA CGG ATG CTA CCG CGC GGT GGC AGC ATA CTC CTA TAT ATC GTG GCC CAA AGG CGC GCC T |
| 3 | MS3 (Bi-methyl.) Bottom strand | AGG CGC GCC TTT GGG CCA CGA TAT ATA GGA GTA TGC TGC CAC CG$^{m5}$C GCG GTA GCA TCC GTT CCC TTG TTG CAC ATA ACA GGG CGC GCC T |
| 4 | MS3 (Bi-methyl.) Top strand | AGG CGC GCC CTG TTA TGT GCA ACA AGG GAA CGG ATG CTA CCG $^{m5}$CGC GGT GGC AGC ATA CTC CTA TAT ATC GTG GCC CAA AGG CGC GCC T |

TABLE 1-continued

Table of sequence listings

| SEQ ID NO: | Description GENE (methyl status) | Sequence (5' to 3')—methylation of C highlighted with "$^{m5}$C" |
|---|---|---|
| 5 | MS3 (fully methyl) Bottom strand | AGG CGC GCC TTT GGG CCA $^{m5}$CGA TAT ATA GGA GTA TGC TGC CAC $^{m5}$CG$^{m5}$C G$^{m5}$CG GTA GCA TC$^{m5}$C GTT CCC TTG TTG CAC ATA ACA GGG CGC GCC T |
| 6 | MS3 (fully methyl) Top strand | AGG CGC GCC CTG TTA TGT GCA ACA AGG GAA $^{m5}$CGG ATG CTA C$^{m5}$CG $^{m5}$CG$^{m5}$C GGT GGC AGC ATA CTC CTA TAT AT$^{m5}$C GTG GCC CAA AGG CGC GCC T |
| 7 | BRCA1 (unmethyl) positive strand | CTG AGA AAC CCC ACA GCC TGT CCC CCG TCC AGG AAG TCT CAG CGA GCT CAC GCC GCG CAG TCG CAG TTT TAA TTT ATC TGT AAT TCC CGC |
| 8 | BRCA1 (unmethyl) positive strand | GCG GGA ATT ACA GAT AAA TTA AAA CTG CGA CTG CGC GGC GTG AGC TCG CTG AGA CTT CCT GGA CGG GGG ACA GGC TGT GGG GTT TCT CAG |
| 9 | BRCA1 (fully methyl) positive strand | CTG AGA AAC CCC ACA GCC TGT CCC C$^{m5}$CG TCC AGG AAG TCT CAG $^{m5}$CGA GCT CA$^{m5}$C GC$^{m5}$C G$^{m5}$CG CAG T$^{m5}$CG CAG TTT TAA TTT ATC TGT AAT TCC CGC |
| 10 | BRCA1 (fully methyl) negative strand | GCG GGA ATT ACA GAT AAA TTA AAA CTG $^{m5}$CGA CTG $^{m5}$CG$^{m5}$C GG$^{m5}$C GTG AGC T$^{m5}$CG CTG AGA CTT CCT GGA $^{m5}$CGG GGG ACA GGC TGT GGG GTT TCT CAG |

TABLE 2

References related to gene fragments

Akiyama, Y., N. Watkins, et al. (2003). "GATA-4 and GATA-5 Transcription Factor Genes and Potential Downstream Antitumor Target Genes Are Epigenetically Silenced in Colorectal and Gastric Cancer" *Molecular and Cellular Biology* 23(23): 8429-8439.
Bachman, K. E., J. G. Herman, et al. (1999). "Methylation-associated Silencing of the Tissue Inhibitor of Metalloproteinase-3 Gene Suggests a Suppressor Role in Kidney, Brain, and Other Human Cancers." *Cancer Res* 59(4): 798-802
Badal, V., L. S. H. Chuang, et al. (2003). "CpG Methylation of Human Papillomavirus Type 16 DNA in Cervical Cancer Cell Lines and in Clinical Specimens: Genomic Hypomethylation Correlates with Carcinogenic Progression." *Journal of Virology* 77(11): 6227-6234.
Cho, B., H. Lee, et al. (2003). "Promoter hypomethylation of a novel cancer/testis antigen gene CAGE is correlated with its aberrant expression and is seen in premalignant stage of gastric carcinoma." *Biochemical and Biophysical Research Communications* 307(1): 52-63.
Costello, J., M. Frühwald, et al. (2000). "Aberrant CpG-island methylation has non-random and tumour-type- specific patterns." *Nature Genetics* 24: 132-138.
De Capoa, A., A. Musolino, et al. (2003). "DNA demethylation is directly related to tumour progression: Evidence in normal, pre-malignant and malignant cells from uterine cervix samples." *Oncology Reports* 10(3): 545-549.
Esteller, M., E. Avizienyte, et al. (2000). "Epigenetic inactivation of LKB1 in primary tumors associated with the Peutz-Jeghers syndrome. *Oncogene* 19(1): 164-168.
Esteller, M., P. G. Corn, et al. (2001). "A Gene Hypermethylation Profile of Human Cancer." *Cancer Res* 61(8): 3225-3229.
Esteller, M., J. M. Silva, et al. (2000). "Promoter Hypermethylation and BRCA1 Inactivation in Sporadic Breast and Ovarian Tumors." *Journal of the National Cancer Institute* 92(7): 564-569
Esteller, M., M. Toyota, et al. (2000). "Inactivation of the DNA Repair Gene O6-Methylguanine-DNA Methyltransferase by Promoter Hypermethylation Is Associated with G to A Mutations in K-ras in Colorectal Tumorigenesis." *Cancer Res* 60(9): 2368-2371.
Feinberg, A. P. and B. Vogelstein (1983). "HYPOMETHYLATION OF RAS ONCOGENES IN PRIMARY HUMAN CANCERS." *Biochemical and Biophysical Research Communications* 111(1): 47-54.
Ferguson, A. T., R. G. Lapidus, et al. (1995). "Demethylation of the Estrogen Receptor Gene in Estrogen Receptor-negative Breast Cancer Cells Can Reactivate Estrogen Receptor Gene Expression." *Cancer Res* 55(11): 2279-2283.
Herman, J., J. Graff, et al. (1996). Methylation-specific PCR: A novel PCR assay for methylation status of CpG islands, National Acad Sciences 93: 9821-9826.
Herman, J. G., C. I. Civin, et al. (1997). "Distinct Patterns of Inactivation of p15INK4B and p16INK4A Characterize the Major Types of Hematological Malignancies." *Cancer Res* 57(5): 837-841.
Herman, J. G., F. Latif, et al. (1994). "Silencing of the VHL Tumor-Suppressor Gene by DNA Methylation in Renal Carcinoma." *Proceedings of the National Academy of Sciences of the United States of America* 91(21): 9700-9704.
Kane, M. F., M. Loda, et al. (1997). "Methylation of the hMLH1 Promoter Correlates with Lack of Expression of hMLH1 in Sporadic Colon Tumors and Mismatch Repair-defective Human Tumor Cell Lines." *Cancer Res* 57(5): 808-811.
Kinoshita, H., Y. Shi, et al. (2000). "Methylation of the Androgen Receptor Minimal Promoter Silences Transcription in Human Prostate Cancer." *Cancer Res* 60(13): 3623-3630.
Nakamura, N. and K. Takenaga (1998). "Hypomethylation of the metastasis-associated S100A4 gene correlates with gene activation in human colon adenocarcinoma cell lines." *Clinical & Experimental Metastasis* 16(5): 471-479.
Nakayama, M., M. Wada, et al. (1998). "Hypomethylation Status of CpG Sites at the Promoter Region and Overexpression of the Human MDR1 Gene in Acute Myeloid Leukemias." *Blood* 92(11): 4296-4307.
Ohtanifujita, N., T. Fujita, et al. (1993). "CPG METHYLATION INACTIVATES THE PROMOTER ACTIVITY OF THE HUMAN RETINOBLASTOMA TUMOR-SUPPRESSOR GENE." *Oncogene* 8(4): 1063-1067.
Reu, F. J., D. W. Leaman, et al. (2006). "Expression of RASSF1A, an Epigenetically Silenced Tumor Suppressor, Overcomes Resistance to Apoptosis Induction by Interferons." *Cancer Res* 66(5): 2785-2793.
Smet, C. D., O. D. Backer, et al. (1996). "The Activation of Human Gene MAGE-1 in Tumor Cells is Correlated with Genome-Wide Demethylation." *Proceedings of the National Academy of Sciences of the United States of America* 93(14): 7149-7153.
Suzuki, H., D. N. Watkins, et al. (2004). "Epigenetic inactivation of SFRP genes allows constitutive WNT signaling in colorectal cancer." *Nature Genetics* 36(4): 417-422.
Wu, H., Y. Chen, et al. (2005). "Hypomethylation-linked activation of PAX2 mediates tamoxifen-stimulated endometrial carcinogenesis." *Nature* 438(7070): 981-987.

We claim:

1. A method for separating DNA based on a methylation parameter, said method comprising:
providing a membrane having one or more nanopores, wherein said membrane separates a first compartment from a second compartment and the nanopore is in fluid communication with the first and second compartments;
providing DNA comprising a heterogeneous mixture of DNA molecules having different methylation parameters to said first compartment;
separating said DNA by establishing an electric field across the membrane, and
generating a threshold voltage across said nanopore from said electric field to force methylated DNA having the methylation parameter through said nanopore from said first to said second compartment without substantially allowing unwanted DNA not having the methylation parameter to pass to said second compartment to concentrate methylated DNA having the methylation parameter in said second compartment by a factor that is greater than or equal to 1000 the number of DNA not having the methylation parameter in said second compartment.

2. The method of claim 1 wherein said methylation parameter is methylation content, methylation pattern, or methylation content and pattern.

3. The method of claim 2 wherein said methylation parameter is methylation content.

4. The method of claim 3, wherein said method is capable of separating DNA differing by one methylation site per 100 bp length of DNA.

5. The method of claim 1, wherein said DNA comprises at least a portion of a gene.

6. The method of claim 5, wherein methylation of said gene is associated with a disease state.

7. The method of claim 6, wherein said disease state is cancer.

8. The method of claim 6, wherein said gene is selected from a group consisting of:
BRCA1 (breast cancer 1 gene);
MS3 (male-sterile gene); and
fragments thereof.

9. The method of claim 1, wherein said membrane comprises silicon nitride ($Si_3N_4$).

10. The method of claim 1, wherein said membrane has a thickness that is selected from a range that is greater than or equal to 10 nm and less than or equal to 50 nm.

11. The method of claim 1, wherein said pore diameter is less than or equal to the effective diameter of linear DNA.

12. The method of claim 1, wherein said pore diameter is selected from a range that is greater than or equal to 1.5 nm and less than or equal to 3 nm.

13. The method of claim 12 wherein said pore diameter is selected from a range that is greater than or equal to 1.6 nm and less than or equal to 2.5 nm.

14. The method of claim 12, wherein said pore has a pore geometry comprising a cone angle, a minimum diameter, a maximum diameter, and a thickness, wherein said pore geometry is selected to generate a force on a DNA molecule within the pore that is sufficient to stretch the DNA.

15. The method of claim 1, wherein said electric field is selected to generate said threshold voltage that is capable of forcing DNA having a methylation content that is equal to or greater than a user-selected methylation content.

16. The method of claim 1, wherein said threshold voltage is selected to measure said methylation parameter.

17. The method of claim 16, wherein said methylation parameter is the number of methylated sites on said DNA.

18. The method of claim 1, wherein said DNA is double stranded and has a sequence length that is selected from a range that is greater than or equal to 50 base pairs.

19. The method of claim 18, wherein said sequence length is selected from a range that is greater than or equal to 50 base pairs and less than or equal to 1000 base pairs.

20. The method of claim 1, further comprising:
analyzing at least a portion of DNA from said second compartment.

21. The method of claim 20, wherein said analyzing step comprises DNA sequencing by polymerase chain reaction.

22. The method of claim 1, further comprising:
sequentially changing said electric field over a plurality of said separating steps to obtain a plurality of individually separated DNA, wherein each separated DNA has a methylation pattern or level different from any other separated DNA.

23. The method of claim 22, wherein said sequentially changing step is used to separate said provided DNA based on methylation level, wherein said DNA comprises a mixture of unmethylated, hemimethylated and methylated DNA.

24. A method of detecting a DNA methylation content or methylation pattern from DNA obtained from a subject, said method comprising:
obtaining a DNA sample from said subject, said DNA sample comprising a heterogeneous mixture of DNA molecules having different methylation content or methylation pattern;
providing a membrane having one or more nanopores, wherein said membrane separates a first compartment from a second compartment and the nanopore is in fluid communication with the first and second compartments;
providing said DNA sample to said first compartment;
establishing an electric field across the membrane, wherein said electric field generates a threshold voltage across said nanopore that is capable of forcing DNA having said methylation content or methylation pattern, without substantially passing DNA not having said methylation content or methylation pattern, through said nanopore from said first to said second compartment to concentrate DNA having said methylation content or methylation pattern in said second compartment by a factor that is greater than or equal to 1000 compared to other DNA in said second compartment not having said methylation content or said methylation parameter; and
detecting said methylation level or pattern by the passage of said methylated content or pattern through said nanopore or by detecting the presence of said methylated content or pattern of DNA in said second compartment.

25. The method of claim 24, wherein said electric field is constant over time.

26. The method of claim 24, wherein said electric field varies over time.

27. The method of claim 24 further comprising determining the methylation content of said DNA by selecting said electric field to generate a force capable of translocating said DNA having a methylation content or greater than a user-selected methylation content through said nanopore, and wherein said force is insufficient to translocated a substantial number of DNA having methylation content lower than said user-selected value.

28. The method of claim 24, wherein said DNA comprises at least a portion of a gene, wherein said gene methylation level or methylation pattern is associated with a disease state.

29. The method of claim 28, wherein said disease state is cancer.

30. The method of claim 24, wherein said subject is a human.

* * * * *